(12) United States Patent
Ursuegui et al.

(10) Patent No.: US 11,708,375 B2
(45) Date of Patent: Jul. 25, 2023

(54) REAGENTS FOR REVERSIBLY PROTECTING BIOLOGICAL MOLECULES

(71) Applicants: BIOMÉRIEUX, Marcy l'Etoile (FR); UNIVERSITÉ DE CAEN NORMANDIE, Caen (FR)

(72) Inventors: Sylvain Ursuegui, Strasbourg (FR); Alain Laurent, Grenoble (FR); Ali Laayoun, La Frette (FR); Frédéric Fabis, Mathieu (FR)

(73) Assignees: BIOMÉRIEUX, Marcy l'Etoile (FR); UNIVERSITÉ DE CAEN NORMANDIE, Caen (FR)

( * ) Notice: Subject to any disclaimer, the term of this patent is extended or adjusted under 35 U.S.C. 154(b) by 1086 days.

(21) Appl. No.: 16/314,824

(22) PCT Filed: Jul. 13, 2017

(86) PCT No.: PCT/FR2017/051925
§ 371 (c)(1),
(2) Date: Jul. 8, 2019

(87) PCT Pub. No.: WO2018/011527
PCT Pub. Date: Jan. 18, 2018

(65) Prior Publication Data
US 2019/0375763 A1    Dec. 12, 2019

(30) Foreign Application Priority Data

Jul. 13, 2016 (FR) ...................... 1656791

(51) Int. Cl.
| | |
|---|---|
| *C07D 265/14* | (2006.01) |
| *C07D 498/04* | (2006.01) |
| *C12P 19/34* | (2006.01) |
| *C12Q 1/6848* | (2018.01) |
| *C12N 9/12* | (2006.01) |
| *C07D 498/00* | (2006.01) |
| *C07D 498/02* | (2006.01) |

(52) U.S. Cl.
CPC ......... *C07D 498/04* (2013.01); *C07D 498/00* (2013.01); *C07D 498/02* (2013.01); *C12N 9/1252* (2013.01); *C12P 19/34* (2013.01)

(58) Field of Classification Search
CPC .. C07D 265/14; C07D 498/04; C12N 9/1252; C12P 19/34; C12Q 1/6848
See application file for complete search history.

(56) References Cited

U.S. PATENT DOCUMENTS

| | | |
|---|---|---|
| 5,677,152 A | 10/1997 | Birch et al. |
| 5,773,258 A | 6/1998 | Birch et al. |
| 2015/0210732 A1 | 7/2015 | Cailly et al. |

FOREIGN PATENT DOCUMENTS

| | | |
|---|---|---|
| EP | 0 771 870 A1 | 5/1997 |
| FR | 1 257 526 A | 3/1961 |
| WO | 2004/052312 A2 | 6/2004 |
| WO | 2008/149168 A1 | 12/2008 |
| WO | 2014/019966 A1 | 2/2014 |
| WO | 2016/003929 A1 | 1/2016 |

OTHER PUBLICATIONS

Lee, "Synthesis of 1-Methyl-3H-1, 4-benzodiazepine-2,5 (1H,4H)-dione and Derivatives," Heterocyclic Chem., Dec. 1964, vol. 1, Issue 5, pp. 235-238.
Louwrier, Ariel et al., "Thermally Reversible Inactivation of TAQ Polymerase in an Organic Solvent for Application in Hot Start PCR" Enzyme and Microbial Technology, vol. 36, pp. 947-952, (2005).
Moorman, A. R. et al., "A New Class of Serine Protease Inactivators Based on Isatoic Anhydride", J. American Chemical Society, vol. 104, pp. 6785-6786, (1982).
Hooker, Jacob M. et al., "Modification of Aniline Containing Proteins Using an Oxidative Coupling Strategy", J. Am. Chem. Soc., vol. 128, pp. 15558-15559, (2006).
Heilbron, Isidor Morris et al., "CCXCII—Chemical Reactivity and Conjugation Part II the Reactivity of the 2-Methyl Group in the 4-Quinazolone Series", Journal of the Chemical Society Transactions, vol. 127, pp. 2167-2175, (1925).
Nagasaka, Tatsuo et al., "Stereoselective Synthesis of Tilivalline", J. Org. Chem. vol. 63, pp. 6797-6801, (1998).
Norcini, G. et al., "Synthesis and Pharmacological Evaluation of Tyramine Congeners Containing Fused Heterocyclic Rings", Eur. J. Med. Chem., vol. 28, pp. 505-511, (1993).
Mar. 12, 2018 Search Report issued in International Patent Application No. PCT/FR2017/051925.
Tedesco, Rosanna et al.,"3-(1,1-Dioxo-2H-(1,2,4)-benzothiadiazin-3-yl)-4-hydroxy-2(1H)-quinolinones, Potent Inhibitors of Hepatitis C Virus RNA-Dependent RNA Polymerase", J Med. Chem., (2006), vol. 49, pp. 971-983.
Dong, Guoqiang et al., "New Tricks for an Old Natural Product: Discovery of Highly Potent Evodiamine Derivatives as Novel Antitumor Agents by Systemic Structure—Activity Relationship Analysis and Biological Evaluations", Journal of Medicinal Chemistry, (2012), vol. 55, pp. 7593-7613.
Online] CAS Registry No. 1871509-91-9, American Chemical Society, Feb. 22, 2016, [retrieved: Jun. 22, 2021].

*Primary Examiner* — Brenda L Coleman
(74) *Attorney, Agent, or Firm* — Oliff PLC

(57) ABSTRACT

The present invention concerns reagents for the reversible protection of biological molecules. It relates in particular to compounds derived from azaisatoic anhydride and their uses for the protection of biological molecules, particularly enzymes, in order to block their activity. The invention also relates to the biological molecules protected in this manner and to the methods for making use of these reagents.

16 Claims, 6 Drawing Sheets

Key: alcool = alcohol

REAGENTS FOR REVERSIBLY PROTECTING BIOLOGICAL MOLECULES

The present invention concerns reagents for the reversible protection of biological molecules. It relates in particular to compounds derived from azaisatoic anhydride and their uses for the protection of biological molecules, particularly enzymes, in order to block their activity. The invention also relates to the biological molecules protected in this manner and to the methods for making use of these reagents.

STATE OF THE ART

Modern diagnostic tests in vitro, using molecular biology techniques for the specific, rapid, and quantitative detection of nucleic acid targets present in a biological sample, most often use polymerase enzymes enabling the amplification of nucleic acid targets from specific primers.

So-called "hot start" polymerases were developed because they offer many advantages compared to their native version, and in particular give better sensitivity performance in diagnostic tests.

The operating principle of a "hot start" polymerase is to temporarily block its activity by an antibody, an aptamer, or a chemical agent, then to restore its activity as soon as the temperature rises during PCR amplification.

Blocking by a chemical agent is particularly advantageous because of its low cost. Inactivation of polymerases by acylation of the amine functional groups of lysine residues has been described in the prior art (for example see. Enzyme and Microbial Technology 36 (2005) 947-952. "Thermally reversible inactivation of Taq polymerase in an organic solvent for implementation in hot start PCR" by Ariel Louwrier, Anne van der Valk) In the denaturation step at 95° C. during the first PCR cycle or in a preactivation step at elevated temperature, the protecting groups are cleaved and the enzyme activity is restored.

U.S. Pat. Nos. 5,677,152 and 5,773,258 disclose the use of citraconic anhydride and its derivatives in an aqueous medium to temporarily protect the $NH_2$ groups of lysines of Taq polymerase. The amide generated after reaction of the anhydride and an amine is then hydrolyzable by the medium acidified after heat treatment in the presence of Tris buffer used in PCR reactions.

It has also been demonstrated that isatoic anhydride derivatives are capable of reacting with nucleophilic groups such as the amines present on proteins. In 1982, Moorman A. R et al. described the acylation of a protein, chymotrypsin, by isatoic anhydride (Moorman A. R., Abeles R. H. J., Am. Chem. Soc., 1982, 104, 6785-6786). This reaction results in inactivation of the protein by generating stable anthranilic derivatives More recently, Hooker et al. used the reactivity of isatoic anhydride to modify the lysine residues of lysozyme molecules and thus introduce aniline motifs which can then be functionalized via an oxidative coupling (Hooker J. M., Esser-Kahn A. B., Francis M. B., J. Am. Chem. Soc., 2006, 106, 1558-1559). Acylation of the amine group present on the side chain of lysines by isatoic anhydride thus leads to the formation of very stable amide bonds.

Patent application FR1257526 describes acylating agents derived from isatoic anhydride for the functionalization, labeling, capture, or separation of ribonucleic acid (RNA) or chimeric nucleic acid (RNA/DNA). The acylating agents are more specifically described for the purpose of fixing the group of interest on these biological molecules.

The present invention proposes providing new reagents for the reversible protection of biological molecules, and in particular for the preparation of "hot start" enzymes, meaning those that can easily be deprotected by heat treatment, said new reagents preferably having one or more of the following advantages:

they are inexpensive, they are stable, they are soluble in aqueous medium.

they are effective in reaction speed, as well as in deprotection speed, the product of their reaction with a biomolecule is stable, they do not require the use of Tris buffer for hot deprotection, and/or they do not generate undesirable side reactions.

The reagents described in the present application are thus particularly suitable for temporarily inactivating the enzymes involved in the polymerization of nucleic acids such as Taq polymerase or certain reverse transcriptases, and more generally enzymes used in in vitro diagnostic techniques.

SUMMARY

Thus, the present invention relates to a compound of the following formula (I).

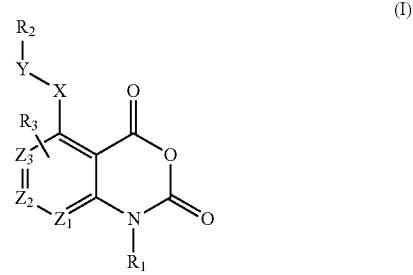

where

X is a covalent bond or a $C_1$-$C_4$ alkyl,

Y is a nucleophilic radical, preferably O, S, $NR_4$, O—$NR_4$, NH—O, or NH—$NR_4$, and $R_4$ is H or a $C_1$-$C_4$ alkyl group, $Z_1$, $Z_2$, $Z_3$ each represent, independently of one another. N or C, preferably $Z_3$ represents C, more preferably $Z_3$ is C and $R_3$ is in position $Z_3$, $R_1$ is H, a substituted or unsubstituted $C_1$-$C_6$ alkyl group, a substituted or unsubstituted alkenyl, a substituted or unsubstituted aryl group, or a substituted or unsubstituted heterocycle, preferably $R_1$ being a methyl or ethyl group.

$R_2$ is a thermolabile and/or acid-labile protecting group, $R_3$ is H, a substituted or unsubstituted $C_1$-$C_{12}$ alkyl group, for example an isopropyl, isobutyl, sec-butyl, tert-butyl, isopentyl, or 2,2-dimethylpropyl group, a substituted or unsubstituted aryl group, a substituted or unsubstituted heterocycle, an acyl group, a substituted or unsubstituted alkenyl group, a halogen (for example F, Cl, Br and I), or a cyano group.

In a preferred embodiment, the compound according to the invention is of the following formula (II):

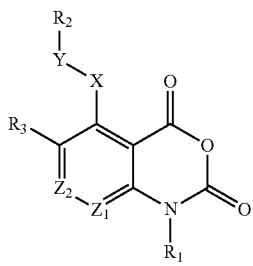
(II)

where X, Y, $Z_1$, $Z_2$, $R_1$, $R_2$ and $R_3$ are as defined above for formula (I).

In one specific embodiment, the thermolabile and/or acid-labile group $R_2$ in formulas (I) and (II) above is selected from the tert-butoxycarbonyl (BOC), substituted or unsubstituted phenoxyacetyl, trityl, methoxytrityl, dimethoxytrityl, or citraconyl groups.

In another particular embodiment, which may be combined with the preceding embodiments, $R_1$ is a methyl group.

In another specific embodiment, possibly combined with the preceding embodiments, $R_3$ is iodine.

In another particular embodiment, which may be combined with the preceding embodiments, $Z_1$ is N and $Z_2$ is C.

In particular, the invention relates to one of the compounds having the following structures'

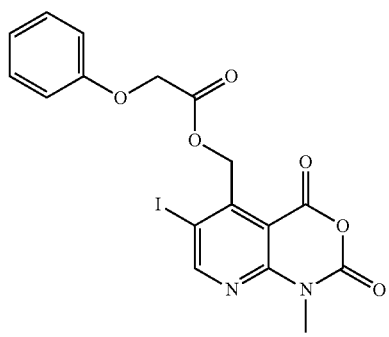
(IV)

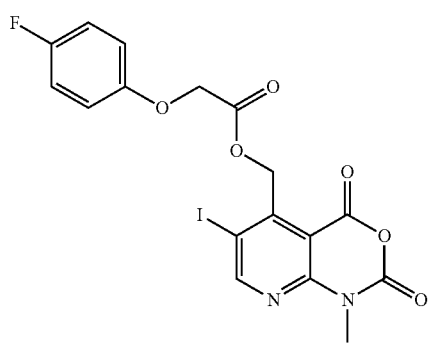
(V)

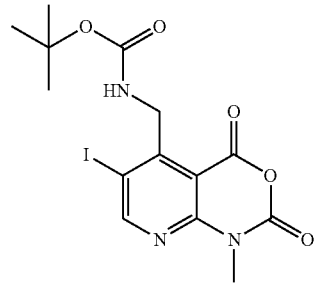
(VI)

The invention also relates to a method for preparing a protected biological molecule, comprising the placing of a compound of the invention as described above in contact with a biological molecule comprising one or more nucleophilic groups, under conditions permitting the acylation of one or more nucleophilic groups of said biological molecule in order to form a protected biological molecule.

In a particularly preferred embodiment, the biological molecule comprises amine functional groups. In particular, the biological molecule is a protein which comprises nucleophilic functional groups, particularly amine functional groups of its lysine residues or of the terminal amino acid, the alcohol functional groups of serines, and/or the thiol functional groups of cysteines.

The invention particularly relates to a protected biological molecule represented by the following formula (III):

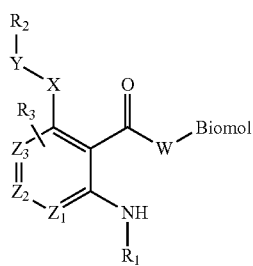
(III)

where
Biomol is a biological molecule,
W is a nucleophilic radical of the biological molecule, preferably NH, S, or O; and
X is a covalent bond or a $C_1$-$C_4$ alkyl,
Y is a nucleophilic radical, preferably O, S, $NR_4$, O—$NR_4$, NH—O, or NH—$NR_4$, and $R_4$ is H or a $C_1$-$C_4$ alkyl group,
$Z_1$, $Z_2$, $Z_3$ each represent, independently of one another, N or C, preferably $Z_3$ represents C, more preferably $Z_3$ is C and $R_3$ is in position $Z_3$,
$R_1$ is H, a substituted or unsubstituted $C_1$-$C_6$ alkyl group, a substituted or unsubstituted alkenyl, a substituted or unsubstituted aryl group, or a substituted or unsubstituted heterocycle, preferably $R_1$ being a methyl or ethyl group,
$R_2$ is H or a thermolabile and/or acid-labile protecting group,
$R_3$ is H, a substituted or unsubstituted $C_1$-$C_{12}$ alkyl group, for example an isopropyl, isobutyl, sec-butyl, tert-butyl, isopentyl, or 2,2-dimethylpropyl group, a substituted or unsubstituted aryl group, a substituted or unsubstituted heterocycle, an acyl group, a substituted or unsubstituted alkenyl group, a halogen (for example F, Cl, Br and 1), or a cyano group.

In one specific embodiment, Biomol is selected from proteins and in particular enzymes.

In a particularly preferred embodiment, Biomol is an enzyme intended for use in a nucleic acid polymerization reaction, for example a DNA polymerase.

Also disclosed are methods for the deprotection of nucleophilic groups of a biological molecule protected by compounds according to the invention, said method comprising a step of cleaving the thermolabile and/or acid-labile group or groups $R_2$, respectively by heat and/or acid treatment, and concomitant deprotection of the nucleophilic groups of the biological molecule.

Thus, the invention also relates to uses of a compound of the invention for the reversible inactivation of an enzyme. In a preferred embodiment, the compound according to the invention is used for the reversible inactivation of an enzyme intended for use in a nucleic acid polymerization reaction, for example a DNA polymerase.

The invention further relates to a method for the amplification of a nucleic acid, comprising the use of a polymerase enzyme inactivated by compounds according to the invention, and at least one heat treatment step at a temperature enabling cleavage of the thermolabile group or groups $R_2$ and deprotection of the nucleophilic groups, said heat treatment step preceding said nucleic acid amplification step.

Definitions

The term "substituted or unsubstituted" means that one or more hydrogen(s) present in a group may be substituted by a functional group, for example selected from the following groups: amine, imine, nitrile, cyano, amide, imide, hydroxyl, alkoxyl, carbonyl, carboxyl, ester, thiol, thioether, thioester, and halide.

The term "Cx-Cy alkyl group" refers to a straight or branched alkyl chain, or a cycloalkyl, having x to y carbon atoms. Examples of a straight alkyl chain include: methyl, ethyl, n-propyl, n-butyl, n-pentyl, n-hexyl, n-heptyl, n-octyl, n-nonyl, and n-decyl. Examples of a branched alkyl chain include: isopropyl, isobutyl, sec-butyl and tert-butyl, isopentyl, 2,2-dimethylpropyl, iso-octyl, iso-nonyl, and iso-decyl Examples of a cycloalkyl include cyclopentyl, cyclohexyl, cycloheptyl, and cyclooctyl.

The term "aryl" refers to aromatic cyclic hydrocarbons containing no heteroatoms in the ring. For example, the aryl group may comprise between 6 and 14 carbon atoms in the aromatic ring portion. Examples of an aryl group include: phenyl, biphenyl, phenanthrenyl, pyrenyl, chrysenyl, anthracenyl, and naphthyl.

The term "heterocycle" refers to a group comprising at least one ring, saturated or unsaturated, in which at least one of the ring atoms is a heteroatom, for example such as N, O, or S. A heterocycle may be composed of multiple condensed rings. For example, the heterocycle may comprise between 6 and 14 atoms in the ring portion.

The term "acyl" refers to a group comprising a carbonyl group, the acyl group being bonded to the molecule via the carbon atom of the carbonyl. This carbon atom is also bonded to another carbon atom belonging to a substituted or unsubstituted alkyl group, a substituted or unsubstituted aryl group, or a substituted or unsubstituted heterocycle. For example, the acyl group comprises between 2 and 12 carbon atoms.

The term "alkenyl" refers to a straight or branched alkyl chain, or a cycloalkyl, comprising at least one carbon-carbon double bond. Examples of alkenyl groups include: vinyl. —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, cyclohexenyl, cyclopentenyl, cyclohexadienyl, butadienyl, pentadienyl, and hexadienyl. For example, the alkenyl group comprises between 2 and 12 carbon atoms.

The term "nucleophile" or "nucleophilic group" refers to a group capable of forming a covalent bond with a reactive site (electrophilic) by providing the two electrons required for the creation of the bond, under suitable reaction conditions. One or more nucleophilic groups may naturally be present in a biological molecule, for example the amine group of a lysine, the amine-terminus of a polypeptide chain, the alcohol of a serine, or the thiol group of a cysteine present in a protein or an enzyme.

The term "protecting group" refers to a functional group introduced into a molecule from a chemical functional group, in order to mask some or all of its reactivity Masking (protecting) a chemical functional group on the molecule thus improves the selectivity of subsequent reactions. The term "protection" or "protected" thus refers to the state of the molecule after reaction with a protecting group. A "protected biological molecule" is a biological molecule that has one or more chemical functional groups protected by protective groups. For enzymes, a protected enzyme can then be inactive. Deprotection refers to the step of releasing some or all of the protective groups from a protected molecule, and preferably obtaining the molecule in its original state prior to its protection by the compounds of the invention.

The term "thermolabile protecting group" refers to a protecting group which is stable at room temperature, for example between 15° C. and 25° C. and which is cleaved, dissociated, or salted out from a molecule to which it is bonded, by thermal treatment (heating step), for example by treatment at a temperature comprised between 50 and 100° C., particularly in the presence of a buffer suitable for the optimal functioning of a biological molecule, for example an enzyme.

Thermolabile protecting groups include in particular those described by Koukhareva et al, *Anal. Chem.*, 2009, 81, 4955-4962, or Trinlink Biotechnologies (WO2012/09434 and U.S. Pat. No. 8,133,669).

Examples of thermolabile protecting groups generally include amides, ethers, esters, acetals, carbonates, thioethers, thioesters, thioacetals, thiocarbonates and particularly those described in Koukhareva et al, *Anal. Chem.*, 2009, 81, 4955-4962, or monomethoxytrityl (MMT), dimethoxytrityl (DMT), and/or substituted or unsubstituted phenoxyacetate.

The term "acid-labile protecting group" refers to a protecting group which is stable in neutral or basic conditions, and which is cleaved, dissociated, or salted out, in acid conditions at room temperature, for example by treatment at a pH below 6.0, or even below 5.0. Examples of acid-labile protecting groups include in particular citraconyl, tert-butoxycarbonyl (BOC), benzyloxycarbonyl, trityl (Trt), methoxytrityl, dimethoxytrityl, benzyloxymethyl (Bom), or t-butoxymethyl (Bum). Other examples of acid-labile protecting groups are described in Chem. Rev., 2009, 109 (6), pp 2455-2504, and more particularly in pages 2467 and 2493 depending on whether it is a protecting group of a hydroxyl or amine functional group.

The term "biological molecule" is broadly understood to include all macromolecules synthesizable by biological organisms. In particular, the term includes nucleic acid polymers and in particular DNA or RNA, polysaccharides, peptides, polypeptides, and proteins, particularly enzymes.

The terms "polypeptide", "peptide", and "protein" are interchangeable, and refer to polymers or oligomers of amino acids. The amino acids of such a polymer are linked by a peptide bond between a carboxyl group and an amine group of two amino acids. A protein can include multiple polypeptides linked by non-covalent bonds and/or disulfide bridges.

Within the meaning of the invention, the term "amino acids" includes naturally occurring or non-naturally occurring amino acids or their substituted derivatives.

Reagents for the Protection of Biological Molecules

The compounds of the invention or reagents for the protection of biological molecules are isatoic anhydride derivatives useful for temporarily protecting ("reversible" protection) nucleophilic groups, such as amines, of a biological molecule, for example a protein.

The compounds of the invention react with the nucleophilic group of a biological molecule and in particular a protein. For example, they can react with the amine E of a lysine of a protein (or enzyme) or the N-terminal amine of a protein (or enzyme), the alcohol of a serine of a protein (or enzyme), or the thiol of a cysteine of a protein, to form an amide, ester, or thioester bond respectively. Among the nucleophilic functional groups of a protein or an enzyme, preferably at least one contributes in an essential manner to maintaining the conformation of the protein and/or of the enzyme functional group. Protecting said essential nucleophilic functional group (for example a lysine, serine, or cysteine) thus causes inactivation of the protein or enzyme.

Advantageously, the amide, ester, and/or thioester bond thus obtained between the biological molecules and the compounds of the invention is particularly stable at low temperatures or room temperature. Biological molecules can be rendered inactive with the compounds of the invention for example under room temperature conditions for storage or transport. More particularly, it is possible to control the starting point of an enzymatic reaction by inducing conditions for the deprotection of an enzyme, according to the following principle:
- In a first step, reacting the compounds of the invention by acylation reaction of the nucleophilic groups of the enzyme with the compound, and obtaining a protected enzyme.
- In a second step, deprotecting a nucleophilic functional group of the compound of the invention, by acid and/or heat treatment, by cleaving a thermolabile and/or acid-labile protecting group present on the compound of the invention and protecting said nucleophilic functional group of the compound of the invention.
- In a third step, obtaining cyclization between the deprotected nucleophilic functional group of the compound of the invention and the carbonyl of the amide, ester, or thioester obtained by acylation of the enzyme, which concomitantly enables reversal of the acylation, deprotection of the enzyme, and restoration of the enzymatic activity.

Unless clarified below in the following text, the term "compounds of the invention" refers to compounds of formula (I) below as well as all their specifically described sub-formulas (and in particular formulas (II) to (VI)), the salts of these compounds, their stereoisomers (including diastereomers and enantiomers), tautomers, and isotope-labeled compounds (including substitutions with deuterium and with radioactive isotopes).

The compound of the invention of formula (I) below

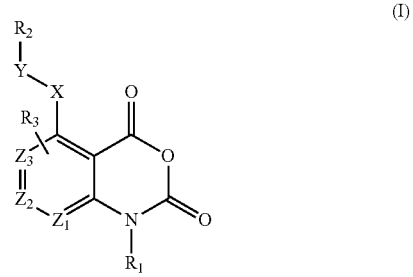

presents in particular
- an azaisotoic anhydride motif enabling acylation of the nucleophilic groups of a molecule,
- a nucleophilic functional group Y protected by a thermolabile and/or acid-labile group $R_2$ and allowing, once released, cleavage of the amide bond generated by acylation,
- a connecting arm X between the isatoic anhydride and the nucleophilic functional group, designed so that it promotes cyclization after deprotection of the nucleophilic functional group,
- a thermolabile and/or acid-labile protecting group $R_2$ of the nucleophilic group Y enabling the release of the nucleophilic functional group Y during the heating and/or acid treatment step and thus allowing intramolecular cyclization,
- preferably, a sterically bulky group $R_3$ enabling steric hindrance around the nucleophile and acceleration of the intramolecular cyclization kinetics. It has fortuitously been discovered that the presence of such steric hindrance greatly benefits the kinetics of intramolecular cyclization and thus the speed of the deprotection of nucleophilic groups of biological molecules.

Thus, an object of the present invention is a compound of the following formula (I):

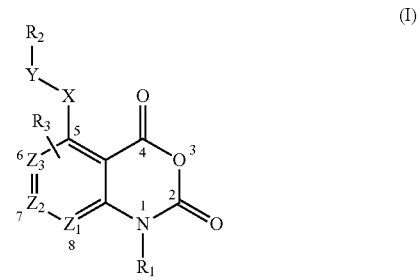

where
X is a covalent bond or a $C_1$-$C_4$ alkyl.
Y is a nucleophilic radical,
$Z_1$, $Z_2$, $Z_3$ each represent, independently of one another, N or C, preferably $Z_3$ represents C, more preferably $Z_3$ is C and $R_3$ is in position $Z_3$,
$R_1$ is H, a substituted or unsubstituted $C_1$-$C_6$ alkyl group, a substituted or unsubstituted alkenyl, a substituted or unsubstituted aryl group, or a substituted or unsubstituted heterocycle. $R_1$ preferably being a methyl or ethyl group.
$R_2$ is a thermolabile and/or acid-labile protecting group,
$R_3$ is H, a substituted or unsubstituted $C_1$-$C_{12}$ alkyl group, for example an iso-propyl, isobutyl, sec-butyl, tert-butyl, isopentyl, or 2,2-dimethylpropyl group, a substituted or unsubstituted aryl group, a substituted or unsubstituted heterocycle, an acyl group, a substituted or unsubstituted alkenyl group, a halogen (for example F, Cl, Br and I), or a cyano group.

Preferably, only one of the radicals $Z_1$, $Z_2$ and $Z_3$ is N.

In one particular embodiment, X is an unsubstituted $C_1$-$C_3$ alkyl for example a methyl.

In one embodiment, $R_1$ is H, a $C_1$-$C_6$ alkyl group, an alkenyl, an aryl group, or a heterocycle, said alkyl, alkenyl, aryl groups or heterocycle possibly being substituted by one or more functional groups selected among nitrile, cyano, amide, imide, alkoxy, carbonyl, carboxyl, ester, thioether, thioester, and halide.

In one embodiment, $R_1$ is a $C_1$-$C_6$ alkyl group possibly substituted by one or more functional groups selected from nitrile, cyano, amide, imide, alkoxy, carbonyl, carboxyl, ester, thioether, thioester and halide.

In one embodiment, $R_2$ is a protecting group selected from amides, ethers, esters, acetals, carbonates, thioethers, thioesters, thioacetals, thiocarbonates, monomethoxytrityl (MMT), dimethoxytrityl (DMT), phenoxyacetate possibly substituted, citraconyl, tert-butoxycarbonyl (BOC), benzyloxycarbonyl, trityl (Trt), methoxytrityl, dimethoxytrityl, benzyloxymethyl (Bom), or t-butoxymethyl (Bum).

In one embodiment, $R_3$ is H, a $C_1$-$C_{12}$ alkyl group, an aryl group, a heterocycle, an acyl group, an alkenyl group, a halogen (for example F, Cl, Br and I), or a cyano, said alkyl, aryl, heterocycle, or alkenyl groups possibly being substituted by one or more functional groups selected from the nitrile, cyano, amide, imide, alkoxy, carbonyl, carboxyl, ester, thioether, thioester, and halide groups.

In one embodiment, $R_3$ is a $C_1$-$C_{12}$ alkyl group or a halogen (for example F, Cl, Br and I), said alkyl group possibly being substituted by one or more functional groups selected from the nitrile, cyano, amide, imide, alkoxy, carbonyl, carboxyl, ester, thioether, thioester, and halide groups.

$R_3$ is placed so as to facilitate cyclization kinetics. For example, in one embodiment, $R_3$ is preferably in position 6.

In one particular embodiment, $R_3$ is a tert-butyl group, an iso-propyl group, a cyano group, or an iodine atom.

In one particular embodiment, Y is different from S—S. In another particular embodiment, the nucleophilic divalent radical Y is selected from O, S, $NR_4$, O—$NR_4$, NH—O, NH—$NR_4$, C(O)—O—$NR_4$, C(O)—NH—O, C(O)—NH—$NR_4$, O—C(O)—NH—$NR_4$, NH—C(O)—NH—$NR_4$, O—C(O)—NH—O, NH—C(O)—NH—O, O—C(O)—O—$NR_4$, NH—C(O)—O—$NR_4$, C(O)—S and $R_4$ is H or a $C_1$-$C_4$ alkyl group.

In one embodiment, the number of X+Y linear atoms, meaning the number of atoms in the main chain connecting the ring to $R_2$ (the different H or $R_4$ substituents not being taken into account) is greater than or equal to 2, for example between 2 and 4.

Preferably, Y is selected from O, S, and NH. In this case, X is not a bond.

In another preferred embodiment, Y is selected from O, S, and $NR_4$, and X is not a bond. In a more preferred embodiment, the compound of the invention is of the following formula (II):

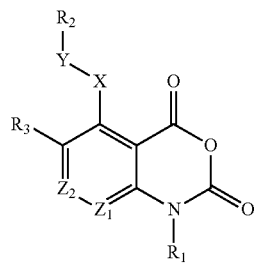

(II)

In one specific embodiment, the thermolabile or acid-labile group $R_2$ in formulas (I) and (II) above is selected from the tert-butoxycarbonyl (BOC), substituted or unsubstituted phenoxyacetyl, trityl, methoxytrityl, dimethoxytrityl, or citraconyl groups.

The thermolabile nature of phenoxyacetate groups has been demonstrated by Lebedev A. et al. (Koukhareva I, Lebedev A, Anal. Chem. 2009, 81, 4955-4962). In one particular embodiment, the protecting group $R_2$ is the thermolabile protecting group phenoxyacetyl, substituted or unsubstituted, preferably it a phenoxyacetyl substituted by a halogen, for example fluorophenoxyacetyl.

The skilled person will be able to identify other thermolabile and/or acid-labile protecting groups $R_2$ that are particularly suitable for the desired function, as described for example in WO2012/094343, U.S. Pat. No. 8,133,669, or in the following books.

Greene's Protective Groups in Organic Synthesis by Peter G. M. Wuts, Publisher: Wiley-Blackwell; Edition: 5th Edition (Dec. 23, 2014), or Protecting Groups by P J Kocienski, Publisher: Thieme Publishing Group; Edition: 3rd Revised edition (Jan. 1, 2005).

In another particular embodiment of the compound according to formula (II), which may be combined with the preceding embodiments. $R_1$ is a methyl group.

In another particular embodiment of the compound according to formula (II), possibly combined with the preceding embodiments, $R_3$ is a halogen, for example iodine.

In another particular embodiment of the compound according to formula (II), which may be combined with the preceding embodiments, $Z_1$ is N and $Z_2$ is C.

In particular, the invention relates to one of the compounds having the following structures, also described in the examples:

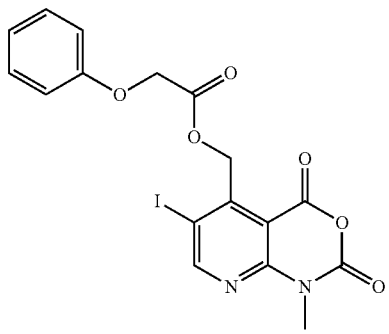

(IV)

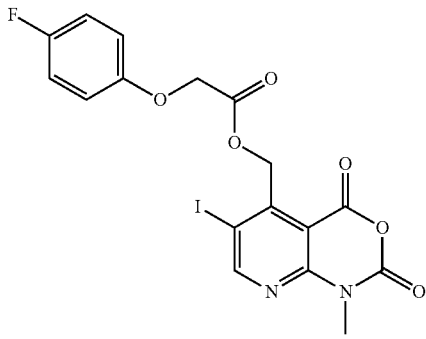

(V)

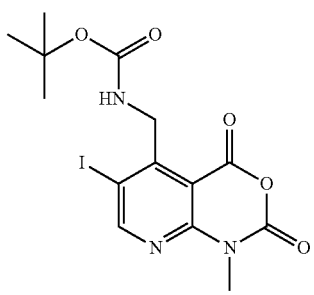

(VI)

Method for Preparing the Compounds of the Invention

The compounds of the invention can be readily synthesized according to methods described in the examples or other synthesis methods known in the prior art.

For example, some of the compounds of the invention according to formula (II) can be synthesized from the precursor hydroxylated compound 6 whose synthesis is described in Example 1. The precursor compound 6 can then be modified by reacting a thermolabile or acid-labile group $R_2$ with the hydroxyl function of the precursor. It is also possible to react the $R_1$ and/or $R_3$ groups with these precursor compounds or their derivatives by conventional chemistry methods. The inventive compound according to formula (II) can finally be obtained by cyclization by nucleophilic substitution, for example as described in step (i) of Diagram 3 in Example 1 below, to yield the compounds of the invention.

Method for Protecting Biological Molecules

The compounds of the invention are useful for the protection, reversible modification or inactivation of enzymes, proteins, and more generally of biological molecules comprising one or more nucleophilic groups, for example biological molecules comprising one or more amines.

The invention relates in particular to a method for preparing a biological molecule comprising one or more protected nucleophilic groups, comprising the placing of a compound of the invention as described above in contact with a biological molecule under conditions permitting the acylation of one or more nucleophilic groups of said biological molecule, to form a biological molecule comprising one or more protected nucleophilic groups (also referred to hereinafter as "protected biological molecule").

The acylation is carried out by nucleophilic substitution on one of the carbonyl functional groups of the anhydride with addition of the nucleophilic group of the biological molecule, and elimination of $CO_2$.

In a particularly preferred embodiment, the biological molecule comprises amine functional groups. In particular, the biological molecule is a protein which comprises ε-amine functional groups of lysine residues or amine of the terminal amino acid. In these embodiments, acylation of the ε-amine functional groups of lysine residues or of the terminal amine allows the formation of very stable amide bonds, particularly in long-term storage conditions (for example more than 24 hours or even several days at room temperature).

As an illustration, the acylation reaction is depicted in Diagram 1 below using a preferred reagent of formula (II) where $R_1$ is a methyl group, $Z_1$ is N, $Z_2$ is C, and $R_3$ is an iodine atom.

Diagram 1 Acylation reaction of the compound of the invention on a biological molecule

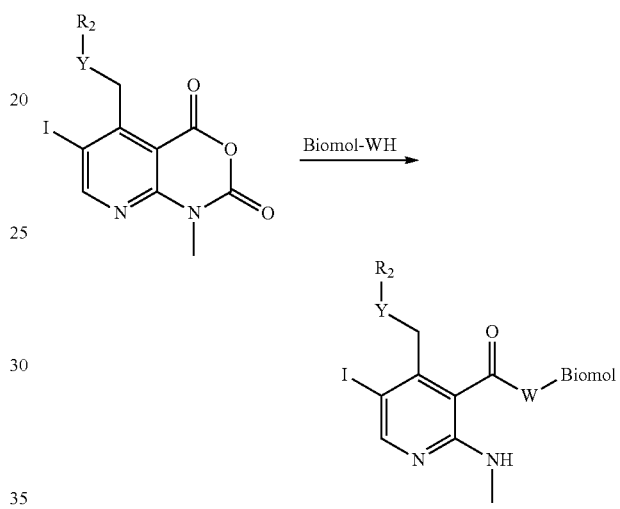

In the case where the biological molecule comprises a plurality of nucleophilic groups to be protected, it is possible to adjust the amount of reagents used according to the degree of modification (protection) desired. In particular, in the case of an enzyme, preferably the degree of modification desired corresponds to the modification threshold beyond which the enzyme is inactivated. This threshold can be determined empirically by simple tests.

The buffer used for the protection reaction is generally a buffer with a pH comprised between 6 and 9, preferably between 7 and 9, more preferably between 7 and 8. Examples of buffers include phosphate buffers, and non nucleophilic buffers operating within this pH range, able to contain up to 50% DMSO. Such buffers are known to the skilled person as is indicated in http://www.sigmaaldrich-.com/life-science/core-bioreagents/biological-buffers.html.

The acylation reaction, particularly acylation of an enzyme with at least one compound of formula (I) or (II), is preferably obtained in a phosphate buffer, for example at pH 7.4.

The protection process is preferably carried out at a temperature comprised between 4° C. and 40° C., for example a temperature comprised between 4° C. and 25° C.

Biological molecules comprising one or more protected nucleophilic groups able to be obtained by the above method are also part of the present invention. In particular, an enzyme may comprise multiple protected amine groups due to the presence of multiple lysines in its polypeptide sequence, or OH or SH groups due to the presence of serine or cysteine, respectively.

The invention therefore concerns a protected biological molecule represented by the following formula (III):

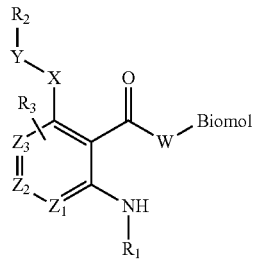

(III)

where
- Biomol is a biological molecule.
- W is a nucleophilic group of the biological molecule, preferably NH, S or O,
- X is a covalent bond or a $C_1$-$C_4$ alkyl.
- Y is a nucleophilic radical, O, S, $NR_4$, O—$NR_4$, NH—O, or NH—$NR_4$, and $R_4$ is H or a $C_1$-$C_4$ alkyl group,
- $Z_1$, $Z_2$, $Z_3$ each represent, independently of one another, N or C, preferably $Z_3$ represents C, more preferably $Z_3$ is C and $R_3$ is in position $Z_3$,
- $R_1$ is H, a substituted or unsubstituted $C_1$-$C_6$ alkyl group, a substituted or unsubstituted alkenyl, a substituted or unsubstituted aryl group, or a substituted or unsubstituted heterocycle, $R_1$ preferably being a methyl or ethyl group,
- $R_2$ is H or a thermolabile and/or acid-labile protecting group,
- $R_3$ is H, a substituted or unsubstituted $C_1$-$C_{12}$ alkyl group, for example an iso-propyl, isobutyl, sec-butyl, tert-butyl, isopentyl, or 2,2-dimethylpropyl group, a substituted or unsubstituted aryl group, a substituted or unsubstituted heterocycle, an acyl group, a substituted or unsubstituted alkenyl group, a halogen (for example F, Cl, Br and I), or a cyano group.

Of course, when the biological molecule comprises multiple nucleophilic groups, for example a protein comprising several lysines, a single biological molecule may comprise some or all of these nucleophilic groups thus protected by acylation with the reagent according to the invention.

In particular, when the reagent of formula (II) is reacted with a biological molecule comprising one or more nucleophilic groups, a protected biological molecule of the following formula (VII) is obtained:

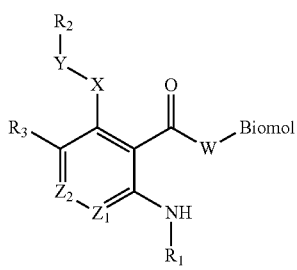

(VII)

By choosing one of the reagents of formula (IV), (V), and (VI) above, protected biological molecules according to one of formulas (VIII), (IX) and (X) are respectively obtained.

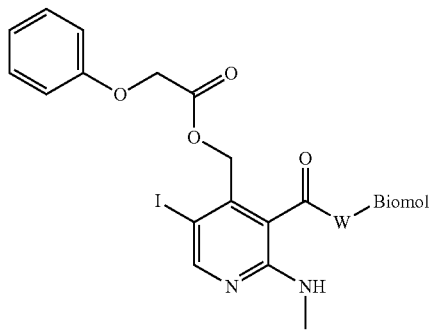

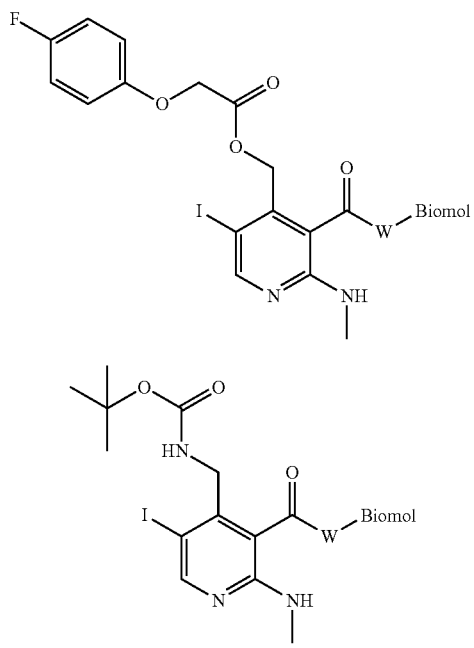

In one specific embodiment, the biological molecule (or Biomol) is chosen from enzymes.

The method is applicable to any type of enzyme. Particular enzymes of interest include the enzymes used in molecular biology techniques, for genetic engineering, or the polymerization of nucleic acids, and more particularly the enzymes used in in vitro diagnostic techniques.

As an illustration, these enzymes include lipases, proteases, glycolases, or nucleases.

In particular, the enzymes of interest include restriction enzymes, ligases, RNA polymerases, DNA polymerases such as DNA polymerase I, II, or III, or DNA polymerase α, β, or γ, terminal deoxynucleotidyl transferase (TdT) or telomerase, DNA-dependent RNA polymerase, primase, or DNA-dependent RNA polymerase (reverse transcriptase).

In a more particularly preferred embodiment, the biological molecule according to the invention is an enzyme intended for use in a nucleic acid polymerization reaction, for example a DNA polymerase. Polymerases suitable for the polymerization of nucleic acids are well known to those skilled in the art. The polymerization reaction is in particular a polymerization reaction in the course of a polymerase chain reaction (PCR) amplification.

In one embodiment, an enzyme of interest used in the protection method according to the invention is selected from the following polymerases: T7 DNA polymerase, Kornberg DNA polymerase, Klenow DNA polymerase, Taq DNA polymerase, Micrococcal DNA polymerase, alpha DNA polymerase, Pfu DNA polymerase, AMV reverse transcriptase, MMLV reverse transcriptase, *E. coli* RNA polymerase, SP6, T3, or T7 RNA polymerase. In particular, in one embodiment, DNA polymerases that are thermostable and/or have an exonuclease activity (for example 3'5' exonuclease) are used in the method according to the invention for the preparation of protected polymerases.

These protected polymerases are particularly useful for hot start applications. Protecting the polymerases prevents non-specific amplification of DNA at low temperatures and thus promotes better efficiency in the amplification reaction, the enzyme being deprotected only at high temperatures by cleavage of the thermolabile group.

Among these thermostable polymerases, we will list in particular those which are not prone to denaturation of their structure and/or inactivation of their enzymatic activity between 50° C. and 100° C., those which function and are active between 50° C. and 100° C. once they are deprotected. Specifically, the polymerases: TAQ Polymerase and Klen TAQ polymerase.

Other thermostable enzymes can be derived from the following biological organisms: *Thermus antranikianii, Thermus aquaticus, Thermus caldophilus, Thermus chliarophilus, Thermus filiformis. Thermus flavus, Thermus igniterrae, Thermus lacteus, Thermus oshimai, Thermus ruber, Thermus rubens, Thermus scotoductus, Thermus silvanus, Thermus* species Z05, *Thermus* species sps-17, *Thermus thermophilus, Thermotoga maritima, Thermotoga neapolitana, Thermosipho africanus, Anaerocellum thermophilum, Bacillus caldotenax, Bacillus stearothermophilus*, etc.

Methods for Using the Compounds of the Invention

Biological molecules protected according to the present invention can advantageously be deprotected by a simple heat and/or acid treatment depending on the $R_2$ group selected.

The principle of deprotection by heat or acid treatment is described in Diagram 2 below with a protected biological molecule (enzyme) according to formula (VII) where $R_1$ is a methyl group, $Z_1$ is N. $Z_2$ is C, and $R_3$ is an iodine atom:

Diagram 2 Example method for the deprotection of a protected biological molecule according to the invention

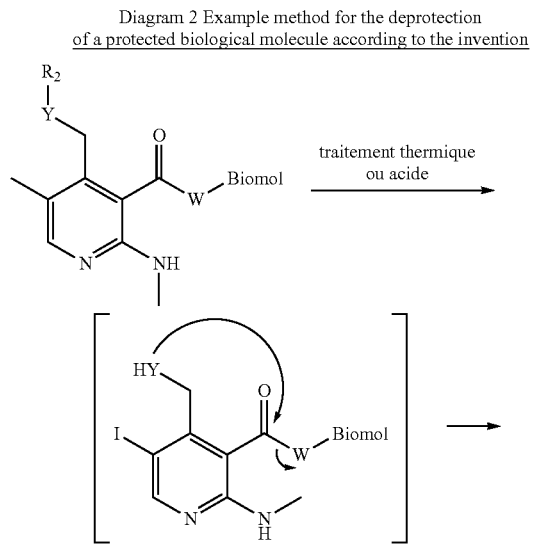

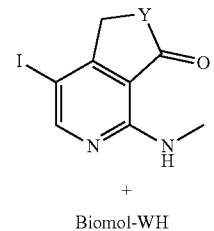

Key: traitement thermique ou acide = Heat or acid treatment

Heat or acid treatment releases the nucleophilic functional group of the compound of the invention by cleaving the thermolabile or acid-labile group. The nucleophilic functional group so released can then allow reversing the acylation by cyclization and deprotection of the biological molecule. Advantageously, the by-product generated by the deprotection reaction is not reactive. In addition, this protection reaction does not require the use of Tris buffer, or a buffer which generates acidic and high-temperature conditions. In particular, the deprotection step can be carried out by heat treatment under conditions with a pH comprised between 6.5 and 9.5, preferably between 8 and 9.0, more preferably between 8.5 and 9.0.

Thus, also described are methods for the deprotection of nucleophilic groups of a biological molecule protected by the compounds of the invention, said method comprising a step of cleaving the thermolabile and/or acid-labile groups $R_2$, by heat and/or acid treatment respectively, and concomitant deprotection of the nucleophilic groups.

One advantage of the method described above is that it allows inactivating the enzymes "Inactivation" is understood to mean that the catalytic activity of an enzyme protected by the method of the invention is greatly reduced or even nonexistent compared to its catalytic activity under optimal activity conditions prior to the protection.

The deprotection method described above then allows restoring the enzymatic activity of the protected enzymes.

The invention therefore also relates to the uses of a compound of the invention for the reversible inactivation of an enzyme. In a preferred embodiment, the compound of the invention is used for the reversible inactivation of an enzyme intended for use in a nucleic acid amplification reaction, for example a polymerase.

The invention is particularly suitable for enzyme hot start applications, for example polymerases used in a nucleic acid amplification reaction (reaction known as "PCR").

Therefore, the invention also concerns a method for amplifying a nucleic acid, comprising (i) the use of a polymerase enzyme protected or inactivated by the compounds of the invention, (ii) at least one step for the deprotection of the polymerase, for example by heat treatment at a temperature allowing cleavage of the thermolabile group or groups $R_2$, (iii) a nucleic acid amplification step using the polymerase deprotected in step (ii).

In one specific embodiment, the amplification method is implemented using a DNA polymerase such as Taq polymerase, Pfu polymerase, T7 polymerase, the Klenow fragment from *E. coli* DNA polymerase and/or a reverse transcriptase, or any other polymerase as described above.

In another embodiment which may be combined with the above, the amplification method is a polymerase chain reaction (PCR reaction), well known to those skilled in the art. The PCR protocol comprises 20 to 40 cycles for example, each cycle comprising at least (i) a denaturation phase of the DNA to be amplified at a temperature generally comprised between 90° C. and 95° C., (ii) a phase of hybridization of the primers with the DNA to be amplified at a temperature generally comprised between 55° C. and 65° C., and (iii) an extension phase at a temperature generally comprised between 68° C. and 75° C.

The protected polymerase according to the invention is in this case preferably a protected thermostable polymerase, for example a Taq (*Thermus aquaticus*) protected polymerase, Pfu (*Pyrococcus furiosus*) protected polymerase, Vent or Tli (*Thermococcus litoralis*) protected polymerase, or their variants, particularly recombinant. Preferably, a sufficient number of amines of said polymerase are protected so that the protected polymerase is inactive or substantially inactive at room temperature and can be deprotected at a temperature equivalent to or greater than the annealing temperature of the primers used for the PCR amplification.

The protected enzymes and polymerases of the invention are also advantageously put to use in variant methods for nucleic amplification by PCR. We list in particular nested PCR, quantitative PCR (or qPCR), semi-quantitative or real time PCR, "error-prone" PCR, or reverse transcription PCR (RT-PCR).

Kits and Toolkits

The invention also concerns kits or toolkits comprising protected enzymes according to the invention, and possibly reagents, buffers, controls, and/or instructions.

In particular, the invention relates to a kit for hot start nucleic acid amplification, comprising
i. a thermostable DNA polymerase protected according to the invention, for example of formula (III), (VII), (VIII), (IX), or (X), where Biomol is a thermostable DNA polymerase,
ii. where appropriate, nucleic acid detection reagents, for example a fluorescent reagent.
iii. where appropriate, a buffer, dNTPs, etc.

These kits are particularly useful for the implementation of amplification methods as described above.

The invention will be better understood with the aid of the examples detailed below and the appended figures.

Top figure (A): Hemoglobin in 8M GuHC

Middle figure (B): Hemoglobin acylated by compound 13 then taken up in 8M GuHCl

Bottom figure (C): Hemoglobin acylated by compound 13 then heated to 95° C. in Tris pH9 and taken up in 8M GuHCl.

Figure 6:
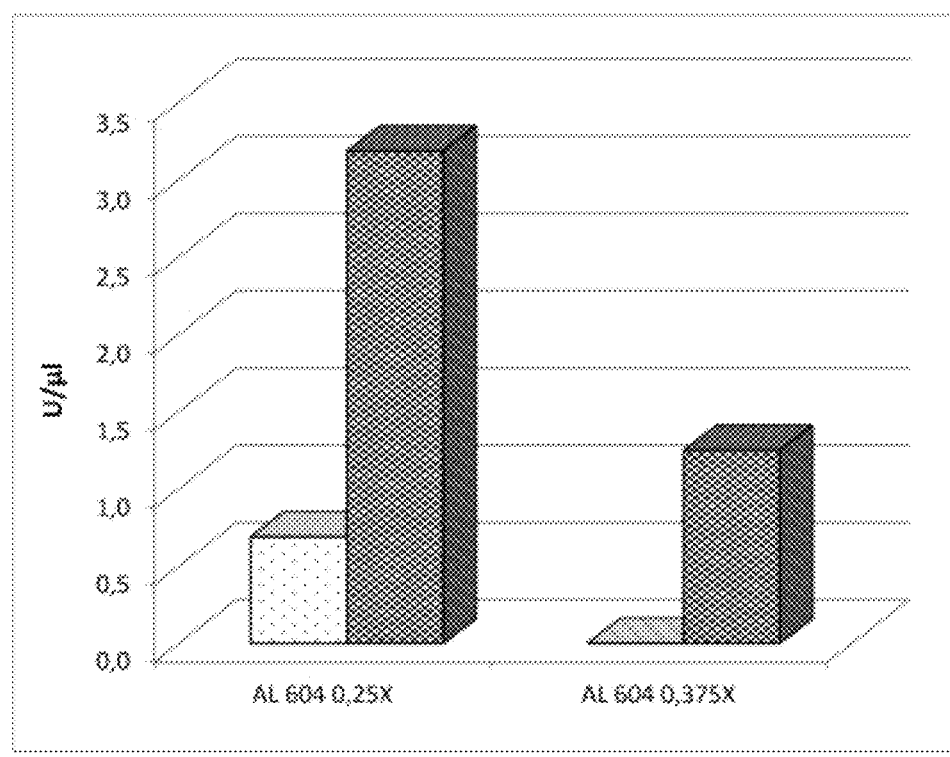

FIG. 6: Inactivation of Taq polymerase following its acylation by compound 13 and restoration of its activity after heat treatment at 95° C. for 15 min under PCR conditions (experiments performed in duplicate, the mean is shown). White with dots on the left: without activation; dark cross-hatched on the right: after 15 minutes of activation at 95° C.

EXAMPLES

In the examples described below, the following abbreviations are used:
ACN: acetonitrile,
AcOEt: ethyl acetate,
$Boc_2O$: di-tert-butyl dicarbonate,
TLC: thin layer chromatography,
$CDCl_3$: deuterated chloroform
d: doublet,
DCM: dichloromethane
dd: doublet of doublets,
DMF: dimethylformamide
DMSO: dimethyl sulfoxide,
DMSO-$d_6$: deuterated dimethyl sulfoxide,
MilliQ water: Ultrapure water (Millipore, Molsheim, France)
EDC: N-Ethyl-N'-(3-dimethylaminopropyl)carbodiimide
eq: equivalent,
PE: petroleum ether,
$Et_2O$: diethyl ether,
HPLC: high performance liquid chromatography,
LCMS: liquid chromatography instrument coupled to a mass spectrometer
HOBt: hydroxybenzotriazole
IA: isatoic anhydride
m: multiplet,
nd: not determined
NIS: N-iodosuccinimide
q: quadruplet,
Yld: Yield,
Rf or RT: retention time
NMR: nuclear magnetic resonance,
s: singlet.
t: triplet.
rt: room temperature
TBDMS: tert-butyldimethylsilyl
TEA: triethylamine
THF: tetrahydrofuran.

General Conditions

The general conditions for the analysis and synthesis of the chemical compounds used in the following examples are described below.

The HPLC analyses are performed with a WATERS 2795 Alliance HPLC system equipped with a PDA 996 diode-array detector (Waters), a ZQ 2000 mass spectrometry detector (Waters), Empower software version 2, and a Waters XTerra MS C18 column (4.6×30, 2.5 μm) used with a flow rate of 1 ml/minute at 30° C. (detection at 260 nm or max plot). The ZQ 2000 mass spectrometer has an Electrospray ionization source. Ionizations are performed in positive mode with a cone voltage of 20V and a capillary voltage of 3.5 kV.

The conditions used for the HPLC analyses are

| Eluent A | Eluent B | Eluent C (Ammonium formiate: AF) | Linear gradient |
|---|---|---|---|
| MilliQ water | ACN | 500 mM AF, pH 7 | 98% A/0% B to 24% A/74% B in 18 min with 2% eluent C in isocratic mode |

The NMR spectra were recorded on a Jeol Lambda 400 MHz spectrometer. The chemical shifts (δ) are given in ppm relative to the peak of the solvent used as the internal reference ($CDCl_3$: 7.26 ppm; DMSO-$d_6$: 2.49 ppm). The spectra are described using the above abbreviations: s, d, t, q, qu, and m. Coupling constants (J) are expressed in hertz (Hz).

The column chromatographies were carried out on Macherey-Nagel Kieselgel 60, mesh 0.063-0.2 mm/70-230, or Merck LiChroprep® RP-18 40-63 μm silica gel.

Analyses by thin layer chromatography were carried out on Macherey-Nagel POLYGRAM® SIL G/UV254, 0.20 mm, or ALUGRAM® RP-18 W/UV254 0.15 mm plates.

Example 1: Synthesis of an Azaisatoic Anhydride Molecule of the Invention Having a O-Phenoxyacetate Thermolabile Protecting Group (9) (Corresponding to Compound IV)

Described in this example is the synthesis of a compound of the invention (according to diagram 3). An initial precursor hydroxylated compound 6 is first synthesized in six steps. It can serve as a starting compound for the synthesis of other compounds of the invention. Compound 6 is then phenoxyacetylated to yield compound 7 then iodized to give compound 8, and finally cyclized to obtain the desired azaisatoic compound 9 capable of reacting with a protein or other biological molecule in order to protect it temporarily.

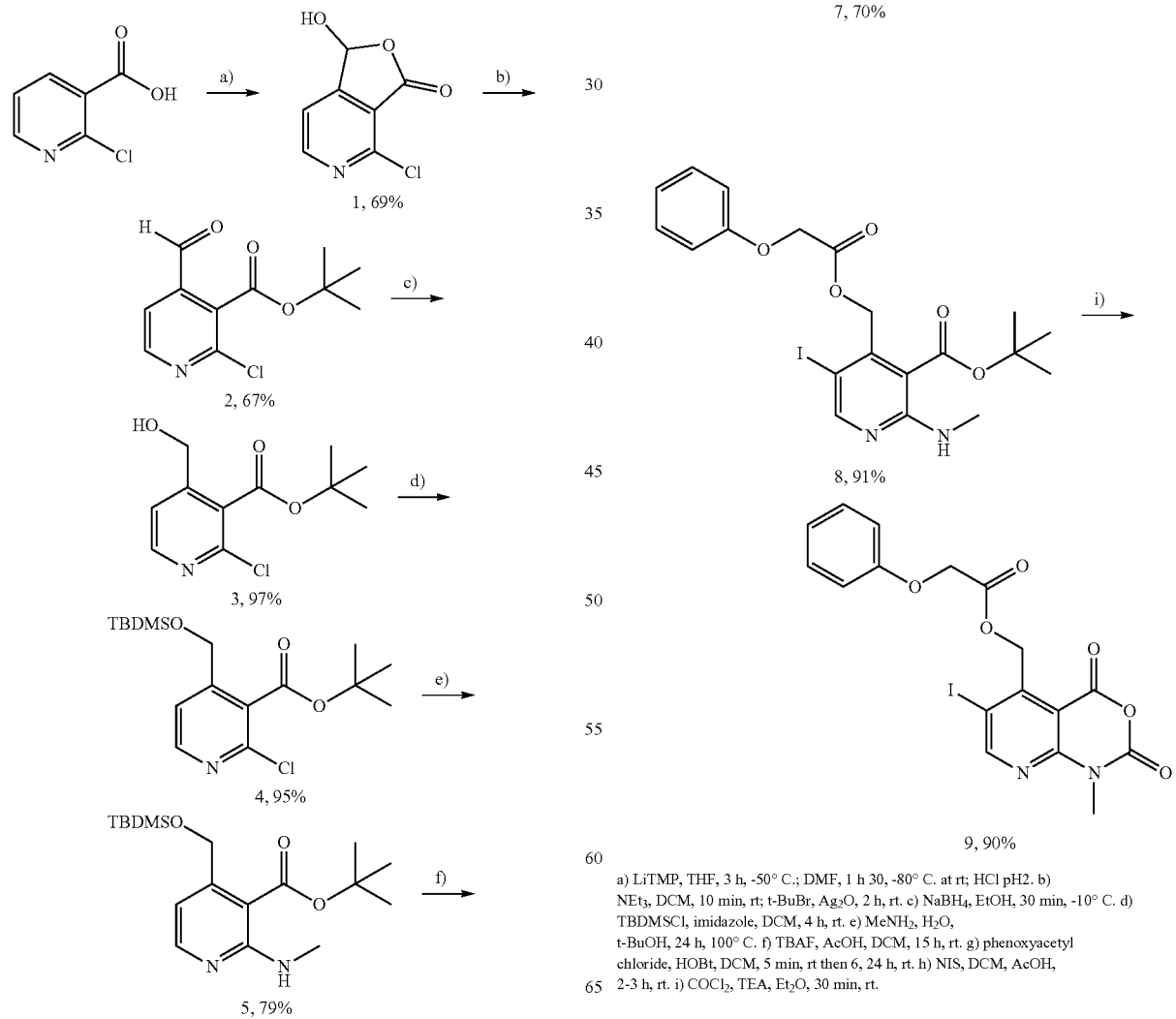

Diagram 3 Synthesis of O-phenoxyacetyl compound 9.

a) LiTMP, THF, 3 h, -50° C.; DMF, 1 h 30, -80° C. at rt; HCl pH2. b) NEt₃, DCM, 10 min, rt; t-BuBr, Ag₂O, 2 h, rt. c) NaBH₄, EtOH, 30 min, -10° C. d) TBDMSCl, imidazole, DCM, 4 h, rt. e) MeNH₂, H₂O, t-BuOH, 24 h, 100° C. f) TBAF, AcOH, DCM, 15 h, rt. g) phenoxyacetyl chloride, HOBt, DCM, 5 min, rt then 6, 24 h, rt. h) NIS, DCM, AcOH, 2-3 h, rt. i) COCl₂, TEA, Et₂O, 30 min, rt.

Example 1.1: Synthesis of 4-chloro-1-hydroxyfuro[3,4-c]pyridin-3(1H)-one (1)

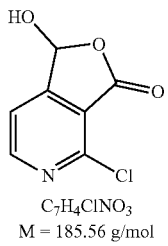

C$_7$H$_4$ClNO$_3$
M = 185.56 g/mol

In a 500 mL Shlenk tube under nitrogen, 19.30 ml 2,2,6,6-tetramethylpiperidine (114.24 mmol, 3 eq) are dissolved in 150 ml THF. At −10° C., 60.13 ml n-BuLi (1.9 M in hexane, 114.24 mmol, 3 eq) are added and the reaction mixture is stirred for 10 min. At −80° C., 6.00 g 2-chloronicotinic acid (38.08 mmol, 1 eq) are added and the reaction is stirred for 3 h at −50° C. 17.69 ml DMF (228.48 mmol, 6 eq) are then introduced at −80° C. and the reaction mixture is stirred for 1 h 30. After returning to room temperature, 100 ml water are added and the solution is extracted with AcOEt (3×150 mL). The aqueous phase is then acidified to pH 2 with concentrated HCl solution and then extracted with AcOEt (3×200 mL). The organic phases are then combined, dried over MgSO$_4$, filtered, and finally evaporated. The resulting oil is then purified on a silica gel column using gradient elution (DCM to DCM/AcOEt 85/15).

The final product is obtained as white powder with a yield of 69% (4.88 g, 26.30 mmol).

Mp=191-193° C.; IR (KBr): ν, 3100 (OH), 2913, 2766, 1776 (C=O), 1609, 1584, 1408, 1194, 1136, 1093, 1047, 925, 755 cm$^{-1}$; $^1$H NMR (400 MHz, DMSO-d$_6$): δ 6.67 (bs, 1H); 7.79 (d, 1H, $^3$J=5.0 Hz); 8.50 (bs, 1H); 8.74 (d, 1H, $^3$J=5.0 Hz); $^{13}$C NMR (100 MHz, DMSO-d$_6$): δ 96.9; 118.8; 120.4; 147.0; 154.6; 159.3; 164.6.

Example 1.2: Synthesis of tert-butyl 2-chloro-4-formylnicotinate (2)

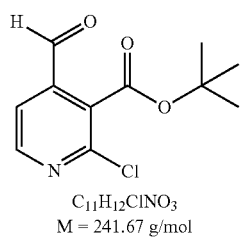

C$_{11}$H$_{12}$ClNO$_3$
M = 241.67 g/mol

To a 250 mL, flask, at room temperature, are added 3.50 g 1 (18.86 mmol, 1 eq), 35 ml DCM, and 2.62 ml TEA (18.86 mmol, 1 eq). The mixture is stirred for 10 min at room temperature. 8.54 ml t-BuBr (75.45 mmol, 4 eq) and 8.74 g Ag$_2$O (37.72 mmol, 2 eq) are then added portionwise at 0° C. The reaction is stirred at room temperature for 2 h. The mixture is filtered through celite, evaporated, and purified on a silica gel column using gradient elution (cyclohexane/AcOEt 95/5 to cyclohexane/AcOEt 90/10). The final product is obtained as a white powder with a yield of 67% (3.07 g, 12.70 mmol).

Mp=97-99° C.; IR (KBr): ν, 3077, 1732 (C=O), 1708 (C=O), 1578, 1370, 1294, 1261, 1178, 1133, 847 cm$^{-1}$; $^1$H NMR (400 MHz, CDCl$_3$): δ 1.64 (s, 9H), 7.65 (d, 1H, $^3$J=5.0 Hz); 8.65 (d, 1H, $^3$J=5.0 Hz); 10.06 (s, 1H); $^{13}$C NMR (100 MHz, CDCl$_3$): δ 27.9 (3C), 85.1; 121.0; 130.1; 140.6; 149.1; 150.9; 163.0; 188.2.

Example 1.3: Synthesis of tert-butyl 2-chloro-4-(hydroxymethyl)nicotinate (i)

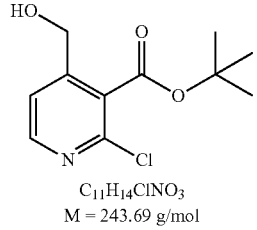 [SMILES: CC(C)(C)OC(=O)c1c(CO)ccnc1Cl]

C$_{11}$H$_{14}$ClNO$_3$
M = 243.69 g/mol

In a 100 mL flask, 3.00 g 2 (12.41 mmol, 1 eq) are dissolved in 35 ml EtOH. At −10° C. 0.51 g NaBH$_4$ (13.65 mmol, 1.1 eq) are added portionwise and the reaction mixture is stirred for 30 min. 50 ml water are then added and the solution is extracted with DCM (3×75 mL). The organic phases are then combined, washed with saturated NaCl solution (2×50 mL), dried over MgSO$_4$, and evaporated.

The final product is obtained as a white powder with a yield of 97% (2.94 g, 12.06 mmol).

Mp=122-124° C.; IR (KBr): ν, 3263 (OH), 3003, 2980, 1717 (C=O), 1592, 1387, 1365, 1299, 1170, 1131, 1080, 1063, 869, 846 cm$^{-1}$; $^1$H NMR (400 MHz, CDCl$_3$): δ 1.60 (s, 9H); 2.89 (t, 1, $^3$J=6.3 Hz), 4.69 (d, 2H, $^3$J=6.3 Hz); 7.39 (d, 1H, $^3$J=5.0 Hz); 8.37 (d, 1H, $^3$J=5.0 Hz); $^{13}$C NMR (100 MHz, CDCl$_3$): δ 27.9 (3C); 61.3; 84.3; 120.6; 128.6; 147.2; 149.8; 150.8; 164.8.

Example 1.4: Synthesis of tert-butyl 4-(((tert-butyldimethyl silyl)oxy)methyl)-2-chloronicotinate (4)

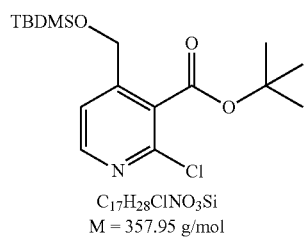 [SMILES: CC(C)(C)OC(=O)c1c(CO[Si](C)(C)C(C)(C)C)ccnc1Cl]

C$_{17}$H$_{28}$ClNO$_3$Si
M = 357.95 g/mol

To a 100 mL flask at room temperature are added 2.25 g 3 (9.23 mmol, 1 eq), 30 ml DCM, 1.88 g imidazole (27.70 mmol, 3 eq), and 2.78 g TBDMSCl (18.47 mmol, 2 eq). The reaction mixture is stirred for 4 h at room temperature. 50 ml water are then added and the solution is extracted with DCM (3×75 mL). The organic phases are then combined, washed with saturated NaCl solution (2×50 mL), dried over MgSO$_4$, and evaporated. The crude reaction product is then purified on a silica gel column using a gradient elution (PE to PE/Et$_2$O 95/5). The final product is obtained as a colorless oil with a yield of 95% (3.15 g, 8.80 mmol).

IR (KBr): ν, 2956, 2931, 2859, 1717 (C=O), 1584, 1369, 1291, 1259, 1168, 1127, 840 cm⁻¹; ¹H NMR (400 MHz, CDCl₃): δ 0.10) (s, 6H); 0.94 (s, 9H); 1.60 (s, 9H), 4.74 (s, 2H); 7.50 (d, 1H, $^3J$=5.0 Hz); 8.39 (d, 1H, $^3J$=5.0 Hz); ¹³C NMR (100 MHz, CDCl₃): δ −5.6 (2C), 18.2; 25.7 (3C), 27.9 (3C); 61.1; 83.6; 119.7; 127.6; 146.7; 149.7; 151.0; 164.1.

Example 1.5: Synthesis of tert-butyl 4-(((tert-butyldimethylsilyl)oxy)methyl)-2-methylamino)nicotinate (5)

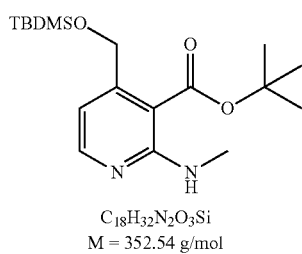 [SMILES: CNc1nccc(CO[Si](C)(C)C(C)(C)C)c1C(=O)OC(C)(C)C]

C₁₈H₃₂N₂O₃Si
M = 352.54 g/mol

Into a sealed tube at room temperature are added 4.00 g 4 (11.17 mmol, 1 eq), 15 ml t-BuOH, and 4.83 ml MeNH₂ (40% w/w in H₂O, 55.87 mmol, 5 eq). The reaction mixture is then stirred for 24 h at 100° C. After evaporation, 50 ml water are then added and the solution is extracted with DCM (3×75 mL). The organic phases are then combined, dried over MgSO₄, and evaporated. The crude reaction product is then purified on a silica gel column using gradient elution (PE to PE/Et₂O 90/10).

The final product is obtained as a colorless oil with a yield of 79% (3.10 g, 8.79 mmol).

IR (KBr): ν, 3377 (N—H), 2931, 2857, 1732 (C=O), 1584, 1370, 1291, 1259, 1190, 1169, 1127, 1112, 839 cm⁻¹; ¹H NMR (400 MHz, CDCl₃): δ 0.11 (s, 6H); 0.96 (s, 9H); 1.59 (s, 9H); 3.02 (d, 3H, $^3J$=4.9 Hz); 4.90 (s, 2H); 6.97 (d, 1H, $^3J$=5.2 Hz); 7.87 (bs, 1H); 8.25 (d, 1H, $^3J$=5.2 Hz); ¹³C NMR (100 MHz, CDCl₃); δ −5.4 (2C); 18.4; 25.9 (4C), 28.4 (3C); 63.9; 82.2; 104.9; 109.0; 151.8; 154.6; 159.5; 167.8.

Example 1.6: Synthesis of tert-butyl 4-(hydroxymethyl)-2-(methylamino)nicotinate (6)

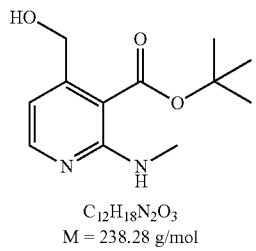 [SMILES: CNc1nccc(CO)c1C(=O)OC(C)(C)C]

C₁₂H₁₈N₂O₃
M = 238.28 g/mol

In a 100 mL flask, 3.00 g of (8.51 mmol, 1 eq) are dissolved in 30 ml DCM. 0.97 ml AcOH (17.02 mmol, 2 eq) and 17.02 ml TBAF (IM in THF, 17.02 mmol, 2 eq) are added simultaneously. The reaction is stirred at room temperature for 15 h. 70 ml water are then added and the solution is extracted with DCM (3×70 mL). The organic phases are then combined, dried over MgSO₄, and evaporated. The crude reaction product is then purified on a silica gel column using gradient elution (PE/AcOEt 80/20 to PE/AcOEt 60/40).

The final product is obtained as a white powder with a yield of 92% (1.86 g, 7.81 mmol).

IR (KBr): ν, 3348 (N—H), 3242 (O—H), 2980, 2944, 1667 (C=O), 1596, 1557, 1530, 1367, 1242, 1165, 1126, 1074, 1061, 805 cm⁻¹; ¹H NMR (400 MHz, CDCl₃): δ 1.60 (s, 9H), 3.01 (d, 3H, $^3J$=4.9 Hz); 4.73 (s, 2H); 6.73 (d, 1H, $^3J$=5.2 Hz); 7.58 (bs, 1H); 8.22 (d, 1H, $^3J$=5.2 Hz); ¹³C NMR (100 MHz, CDCl₃): δ 28.3 (3C), 28.4; 64.0; 83.0; 106.4; 110.7; 151.8; 153.2; 159.2; 167.5.

Example 1.7: tert-butyl 2-(methylamino)-4-((2-phenoxyacetoxy)methyl)nicotinate (7)

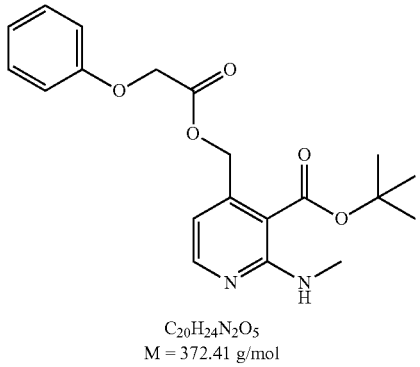 [SMILES: CNc1nccc(COC(=O)COc2ccccc2)c1C(=O)OC(C)(C)C]

C₂₀H₂₄N₂O₅
M = 372.41 g/mol

In a 50 mL flask, 204 µL phenoxyacetyl chloride (1.47 mmol, 1 eq) are dissolved in 5 ml DCM. 198 mg HOBt (1.47 mmol, 1 eq) are added and the reaction mixture is stirred at room temperature After 10 min, 350 mg 6 (1.47 mmol, 1 eq) are added and the reaction is then stirred at room temperature for 24 h. 40 ml water are then added and the solution is extracted with Et₂O (4×30 mL). The organic phases are then combined, dried over MgSO₄, and evaporated. The crude reaction product is then purified on a silica gel column using gradient elution (PE to PE/AcOEt 8/2).

The final product is obtained as a white powder with a yield of 70%, (385 mg, 1.03 mmol).

Mp=149-15° C.; IR (KBr): ν, 3365, 2970, 1760, 1668, 1583, 1192, 752; ¹H NMR (CDCl₃, 400 MHz): δ 1.59 (s, 9H); 3.01 (d, 3H, $^3J$=4.9 Hz); 4.75 (s, 2H); 5.45 (s, 2H); 6.53 (d, 1H, $^3J$=5.1 Hz), 6.94 (m, 2H); 7.01 (t, 1H, $^3J$=7.3 Hz); 7.30 (m, 2H); 7.89 (d, 1H, $^3J$=4.2 Hz); 8.18 (d, 1H, $^3J$=5.12 Hz); ¹³C NMR (CDCl₃, 100 MHz): δ 28.3 (4C); 65.2; 65.4; 83.1; 105.6; 108.9; 114.6 (2C); 121.8; 129.6 (2C), 147.4; 152.0; 157.6; 159.6; 167.1; 168.6.

Example 1.8: tert-butyl 5-iodo-2-(methylamino)-4-((2-phenoxyacetoxy)methyl)nicotinate (8)

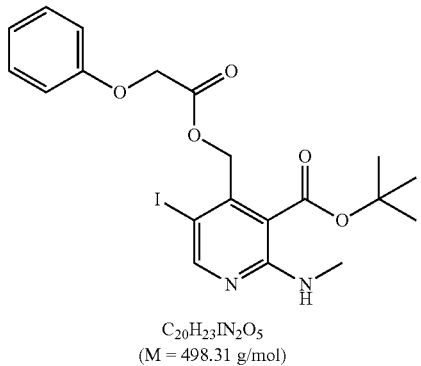 [SMILES: CNc1ncc(I)c(COC(=O)COc2ccccc2)c1C(=O)OC(C)(C)C]

C$_{20}$H$_{23}$IN$_2$O$_5$
(M = 498.31 g/mol)

Into a 25 mL flask are added 280 mg 7 (0.75 mmol, 1 eq), 5 ml DCM, 253 mg NIS (1.12 mmol, 1.5 eq), and 500 µL acetic acid. The reaction mixture is stirred for 3 h at room temperature. The reaction mixture is then neutralized with 20 ml saturated aqueous solution of sodium thiosulfate, taken up in 20 ml saturated solution of NaHCO$_3$, then extracted with Et$_2$O (4×30 mL). The organic phases are then combined, dried over MgSO$_4$, and evaporated. The crude reaction product is then purified on a silica gel column using gradient elution (PE to PE/AcOEt 9/1).

The final product is obtained as a yellow powder with a yield of 91% (340 mg, 0.68 mmol).

Mp=127-129° C.; IR (KBr) ν, 3424, 2934, 1755, 1704, 1576, 1193, 752; $^1$H NMR (CDCl$_3$, 400 MHz): δ 1.56 (s, 9H); 2.97 (d, 3H, $^3J$=4.6 Hz); 4.64 (s, 2H); 5.4 (s, 2H); 6.90 (d, 2H, $^3J$=7.8 Hz); 6.99 (t, 1H, $^3J$=7.3 Hz); 7.27 (m, 2H); 8.50 (s, 1H): the N—H signal is missing; $^{13}$C NMR (CDCl$_3$, 100 MHz): δ 28.1 (3C); 28.4; 65.0; 68.7; 82.5; 83.7; 112.7; 114.6 (2C); 121.8; 129.5 (2C); 144.6; 157.5; 157.7; 158.3; 166.5; 168.3.

Example 1.9: (6-iodo-1-methyl-2,4-dioxo-2,4-di-hydro-1H-pyrido[2,3-d][1,3]oxazine-5-yl) methyl 2-phenoxyacetate (2)

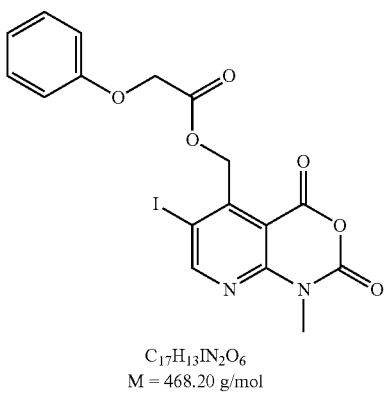 [SMILES: Cn1c(=O)oc(=O)c2c(COC(=O)COc3ccccc3)c(I)cnc21]

C$_{17}$H$_{13}$IN$_2$O$_6$
M = 468.20 g/mol

In a 50 mL flask under nitrogen, 300 mg 8 (0.60 mmol, 1 eq) are dissolved in 10 ml DCM. 951 µL phosgene (20% in toluene, 1.80 mmol, 3 eq) and 251 µL TEA (1.80 mmol, 3 eq) are added simultaneously and the reaction is stirred at room temperature. This is repeated three times to convert all of the raw material. 40 ml water are then added and the solution is extracted with Et$_2$O (5×50 mL). The organic phases are then combined, dried over MgSO$_4$, and evaporated. The reaction mixture is evaporated to dryness and directly purified on a C18-grafted silica gel column, using gradient elution (H$_2$O/ACN 95/5 to H$_2$O/ACN 5/95) The final product is obtained as a white powder with a yield of 90% (255 mg, 0.54 mmol).

Mp=162-164° C.; IR (KBr) ν (cm$^{-1}$): 3439, 2935, 1787, 1757, 1728, 1450, 1176, 756; $^1$H NMR (CDCl$_3$, 400 MHz): δ 3.65 (s, 3H); 4.65 (s, 2H); 5.79 (s, 2H); 6.86 (d, 2H, $^3J$=8.5 Hz); 6.96 (t, 1H, $^3J$=7.5 Hz); 7.27 (m, 2H); 9.00 (s, 1H); $^{13}$C NMR (CDCl$_3$, 100 MHz): δ 31.2; 64.8; 66.7; 94.7; 107.7; 114.6 (2C); 121.8; 129.5 (2C), 146.8; 150.0; 153.3; 155.1; 157.5; 162.7; 168.2.

Example 2: Synthesis of a Type of Azaisatoic Anhydride Molecule of the Invention Having an O-Fluoro-Phenoxyacetate Thermolabile Protecting Group 13 (Corresponding to Compound V)

Described here is the synthesis of another exemplary compound of the invention (according to Diagram 4). The precursor compound 6 is fluoro-phenoxyacetyl (a group which can be more thermolabile) in order to yield compound 11, then iodinated to yield compound 12 and finally cyclized to obtain the azaisatoic compound 13.

Diagram 4 Synthesis of O-fluoro-phenoxyacetyl compound 13.

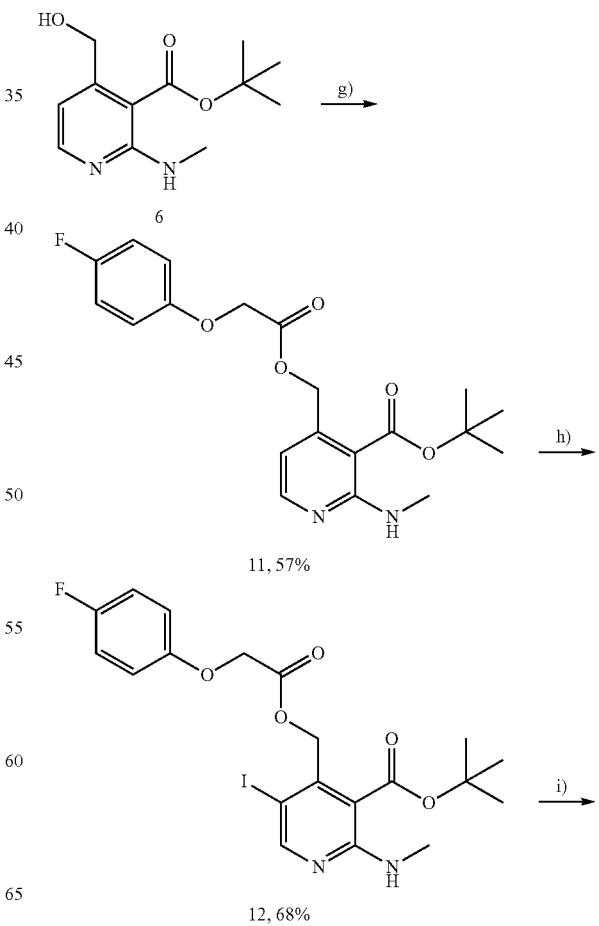

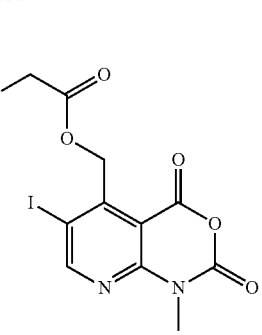

13, 77% g) X = F, 4-fluorophenoxy acetic acid, EDC, HOBt, 5 min, rt then 6, 3 h, rt. h) NIS, DCM, AcOH, 2-3 h, rt. i) COCl2, TEA, Et2O, 30 min, rt.

Example 2.1: tert butyl 4-((2-(4-fluorophenoxy)acetoxy)methyl)-2-(methylamino) nicotinate (11)

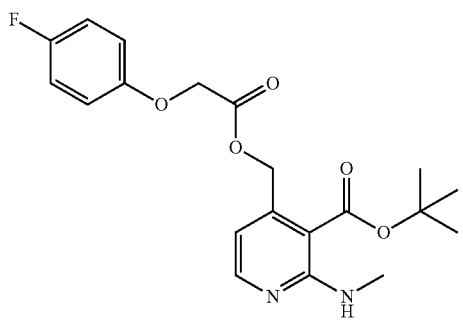

$C_{20}H_{23}FN_2O_5$
M = 390.40 g/mol

Into a 50 mL flask are added 149 mg 4-fluorophenoxy-acetic acid (0.88 mmol, 1.05 eq), 5 ml DCM, 169 mg EDC (0.88 mmol, 1.05 eq), and 119 mg HOBt (0.88 mmol, 1.05 eq). After 5 min at room temperature, 200 mg 6 (0.84 mmol, 1 eq) are added and the reaction is stirred at room temperature for 3 h. 30 ml water are then added and the solution is extracted with Et$_2$O (3×30 mL). The organic phases are then combined, dried over MgSO$_4$, and evaporated. The crude reaction product is then purified on a silica gel column using gradient elution (PE/AcOEt 9/1 to PE/AcOEt 8/2).

The final product is obtained as a yellowish powder with a yield of 57% (190 mg, 0.49 mmol).

Mp=151-153° C.; IR (KBr) ν, (cm-1): 3376, 2977, 2935, 1758 (CO), 1683 (CO), 1586, 1189, 831; 1H NMR (CDCl3, 400 MHz): δ 1.60 (s, 9H); 3.02 (d, 3H, 3J=4.6 Hz); 4.71 (s, 2H); 5.45 (s, 2H), 6.54 (d, 1H, 3J=5.2 Hz); 6.88 (m, 2H); 6.99 (t, 2H, 3J=8.3 Hz); 7.88 (S, 1H); 8.20 (d, 1H, 3J=5.2 Hz); 13C NMR (CDCl3, 100 MHz): δ 28.1; 28.3 (3C); 65.4; 65.9; 83.1; 105.6; 109.0; 115.9 (d, 3JC-F=8 Hz, 2C), 116.0 (d, 2JC-F=23 Hz, 2C); 147.3; 152.0; 153.8 (d, 4JC-F=2 Hz, 1C); 1578 (d, 1JC-F=239 Hz, 1C), 159.5; 167.1; 168.4.

Example 2.2: (6-iodo-1-methyl-2,4-dioxo-2,4-dihydro-1H-pyrido[2,3-d][1,3] oxazine-5-yl) methyl 2-(4-fluorophenoxy)acetate (12)

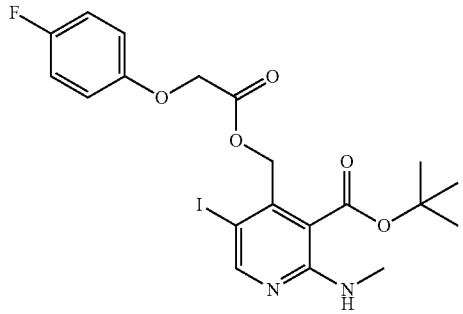

$C_{20}H_{22}FIN_2O_5$
M = 516.30 g/mol

In a 25 ml flask, 200 mg 11 (0.51 mmol, 1 eq) are dissolved in 3 ml DCM. 172 mg NIS (0.77 mmol, 1.5 eq) and 150 μL acetic acid are added and the reaction medium is stirred for 2 h. The reaction mixture is then neutralized with 20 ml saturated aqueous solution of sodium thiosulfate, taken up in 20 ml saturated solution of NaHCO$_3$, then extracted with Et$_2$O (4×30 mL). The organic phases are then combined, dried over MgSO$_4$, and evaporated. The crude reaction product is then purified on a silica gel column using gradient elution (PE to PE/AcOEt 9/1). The final product is obtained as a yellow oil with a yield of 68% (180 mg, 0.35 mmol).

IR (KBr): ν, 3413, 2926, 1763, 1688, 1506, 1183, 828; 1H NMR (CDCl3, 400 MHz): δ 1.56 (s, 9H); 2.97 (d, 3H, 3J=4.64 Hz); 4.60 (s, 2H); 5.37 (s, 2H); 6.85 (m, 2H); 6.96 (m, 2H); 8.50 (s, 1H); 13C NMR (CDCl3, 100 MHz): δ 28.1 (3C), 28.4; 65.7; 68.7; 82.4; 83.7; 112.7; 115.9 (d, 2JC-F=23 Hz, 2C); 116.0 (d, 3JC-F=8 Hz, 2C); 144.5; 153.7; 157.7; 157.8 (d, 1JC-F=239 Hz, 1C); 158.3; 166.4; 168.2.

Example 2.3: (6-iodo-1-methyl-2,4-dioxo-2,4-dihydro-1H-pyrido[2,3-d][1,3]oxazine-5-yl) methyl 2-(4-fluorophenoxy)acetate (13)

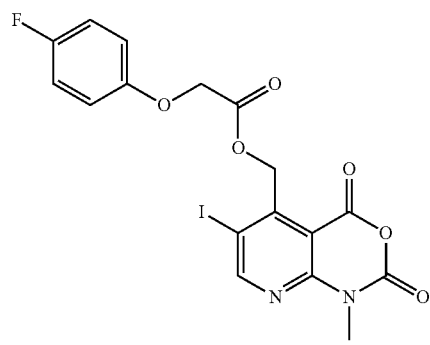

$C_{17}H_{12}FIN_2O_6$
M = 486.19 g/mol

In a 50 mL flask under nitrogen, 160 mg 12 (0.31 mmol, 1 eq) are dissolved in 3 ml DCM. 489 μL phosgene (20% in THF, 0.98 mmol, 9 eq) and 129 μL TEA (0.98 mmol, 9 eq)

are added simultaneously and the reaction is stirred for 30 min. 30 ml water are then added and the solution is extracted with Et$_2$O (3×30 mL). The organic phases are then combined, dried over MgSO$_4$, and evaporated. The reaction mixture is evaporated to dryness and directly purified on a C18-grafted silica gel column, using gradient elution (H$_2$O/ACN 95/5 to H$_2$O/ACN 5/95).

The final product is obtained as a white powder with a yield of 77% (115 mg; 0.24 mmol).

Mp=150-152° C.; IR (KBr) ν (cm-1): 3454, 3078, 2934, 1787, 1745, 1504, 1194, 825; 1H NMR (CDCl3, 400 MHz): δ 3.66 (s, 3H); 4.62 (s, 2H); 5.78 (s, 2H); 6.83 (m, 2H); 6.95 (m, 2H); 9.01 (s, 1H); 13C NMR (CDCl3, 100 MHz): δ 31.2; 65.6; 66.8; 94.7; 107.7; 115.9 (d, 2JC-F=23 Hz, 2C); 115.9 (d, 3JC-F=8 Hz, 2C); 146.7; 150.0; 153.4; 153.7 (d, 4JC-F=2 Hz, 1C); 155.2; 157.8 (d, 1JC-F=239 Hz, 1C); 162.8; 168.1.

Example 3: Synthesis of a Type of Azaisatoic Anhydride Molecule of the Invention Having an N-Boc Acid-Labile/Thermolabile Protecting Group 18 (Corresponding to Compound VI)

Here we describe the synthesis of another exemplary compound of the invention (according to diagram 5). The precursor compound 6 is first converted into azido compound 15 which is a precursor of an amine compound in which the amine functional group is coupled to the BOC protecting group to obtain compound 16. An iodination reaction gives compound 17, and finally cyclization allows access to the azaisatoic compound 18.

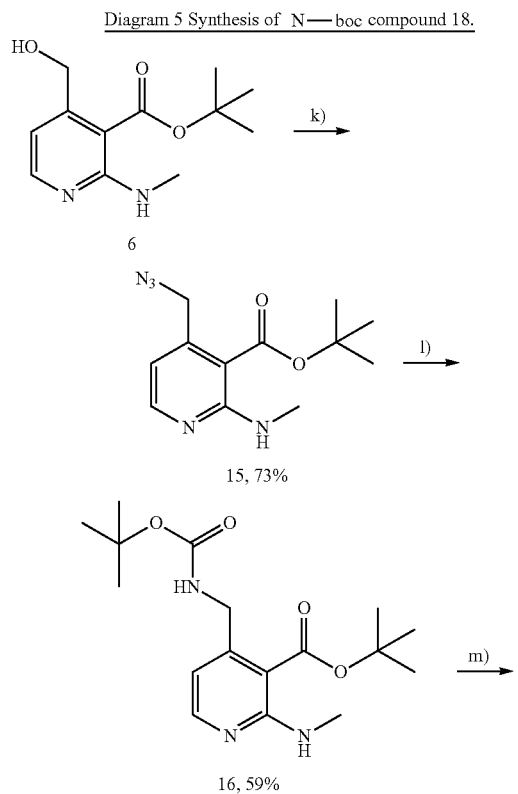

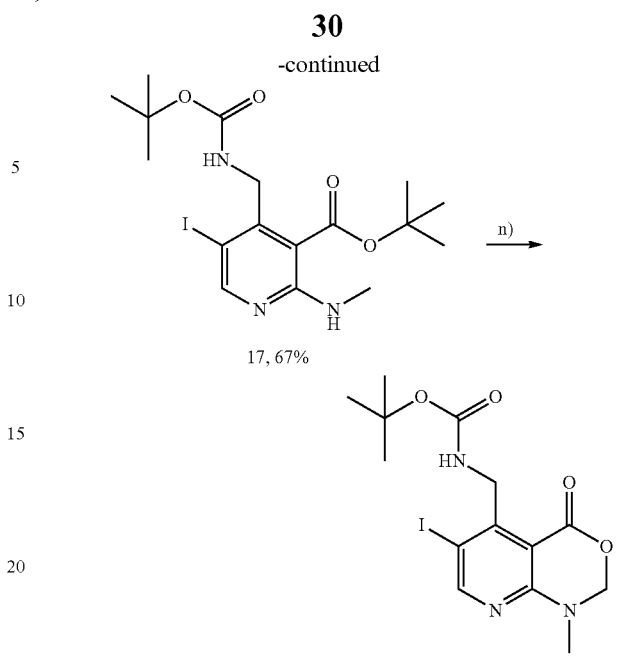

k) MeSO$_2$Cl, NEt$_3$, DCM, 3 h, 0° C. at rt then NaN$_3$, TEA, DCM, 3 h, rt. l) BOC$_2$O, NaOH, PCy$_3$, THF, 2 h, rt. m) NIS, DCM, AcOH, 12 h, rt. n) COCl2, TEA, Et2O, 30 min, rt.

Example 3: tert-butyl 4-(azidomethyl)-2-(methylamino)nicotinate (15)

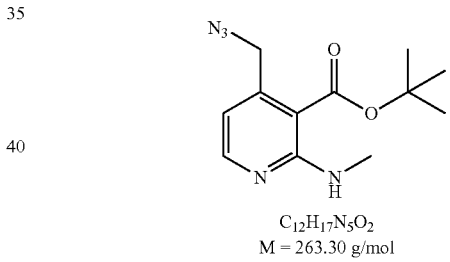

In a 100 mL flask under nitrogen, 1.40 g 6 (5.88 mmol, 1 eq) are dissolved in 20 ml DMF At 0° C., 0.91 ml MeSO$_2$Cl (11.76 mmol, 2 eq) and 4.08 ml TEA (29.3 mmol, 5 eq) are added simultaneously. The reaction mixture is stirred at room temperature and monitoring is performed by TLC (PE/Et$_2$O 1/1). After complete formation of the corresponding mesylate derivative, 1.15 g NaN$_3$ (17.64 mmol, 3 eq) are added and the mixture is stirred for 3 h at room temperature. 50 ml water are then added and the solution is extracted with Et$_2$O (3×60 mL). The organic phases are then combined, dried over MgSO$_4$, and evaporated. The crude reaction product is then purified on a silica gel column using gradient elution (PE/Et$_2$O 9/1 to PE/Et$_2$O 8/2). The final product is obtained as yellow oil with a yield of 73% (1.13 g, 4.29 mmol).

IR (KBr) ν, 3374, 2978, 2104 (N3), 1679, 1586, 1425, 1125, 847, 655; 1H NMR (CDCl3, 400 MHz): δ 1.60 (s, 9H); 3.01 (d, 3H, 3J=5.0 Hz); 4.58 (s, 2H); 6.61 (d, 1H, 3J=5.0 Hz); 7.73 (s, 1H); 8.24 (d, 11H, 3J=5.0 Hz); 13C NMR (CDCl3, 100 MHz): δ 28.3 (3C); 53.9; 77.0; 83.1; 106.7; 111.5; 146.8; 152.0; 159.5; 167.1.

Example 3.1: tert butyl 4-(((tert-butoxycarbonyl)amino)methyl)-2-(methylamino) nicotinate (16)

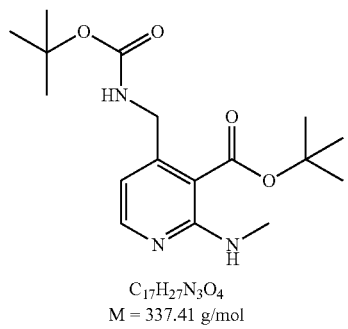 [SMILES: CNc1nccc(CNC(=O)OC(C)(C)C)c1C(=O)OC(C)(C)C]

C$_{17}$H$_{27}$N$_3$O$_4$
M = 337.41 g/mol

In a 25 ml flask, 180 mg 15 (0.68 mmol, 1 eq) and 447 mg Boc$_2$O (2.05 mmol, 3 eq) are dissolved in 5 mL THF. 750 µL aqueous solution of NaOH (0.75 mmol, 1.1 eq, lM in H$_2$O) and 230 mg PCy3 are added in succession. The reaction is stirred at room temperature for 2 h. 30 ml water are then added and the solution is extracted with Et$_2$O (3×30 mL). The organic phases are then combined, dried over MgSO$_4$, and evaporated. The crude reaction product is then purified on a silica gel column using gradient elution (PE/AcOEt 9/1 to PE/AcOEt 8/2). The final product is obtained as yellow oil with a yield of 59% (135 mg, 0.40 mmol).

1H NMR (CDCl3, 400 MHz): δ 1.44 (s, 9H); 1.60 (s, 9H); 3.01 (d, 3H, 3J=4.6 Hz), 4.40 (d, 2H, 3J=6.1 Hz); 5.02 (sl, 1H); 6.57 (d, 1H, 3J=5.1 Hz); 7.52 (sl, 1H); 8.18 (d, 1H, 3J=5.1 Hz); 13C NMR (CDCl3, 100 MHz): δ 28.4 (6C); 28.5; 43.9; 79.6; 83.0; 107.6; 111.6; 150.5; 151.5; 155.7; 159.2; 167.4.

Example 3.2: tert-butyl 4-(((tert-butoxycarbonyl)amino)methyl)-5-iodo-2-(methylamino) nicotinate (17)

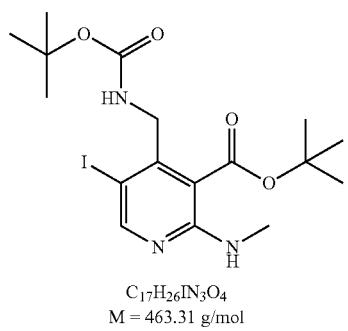 [SMILES: CNc1ncc(I)c(CNC(=O)OC(C)(C)C)c1C(=O)OC(C)(C)C]

C$_{17}$H$_{26}$IN$_3$O$_4$
M = 463.31 g/mol

In a 25 ml flask, 130 mg 16 (0.39 mmol, 1 eq) are dissolved in 4 ml DCM. 225 mg NIS (0.58 mmol, 1.5 eq) and 200 µL acetic acid are added and the reaction mixture is stirred for 12 h. The reaction mixture is then neutralized with 10 mL saturated aqueous solution of sodium thiosulfate, taken up in 10 mL saturated solution of NaHCO$_3$, then extracted with Et$_2$O (4×30 mL). The organic phases are then combined, dried over MgSO$_4$, and evaporated. The crude reaction product is then purified on a silica gel column using gradient elution (PE to PE/AcOEt 9/1).

The final product is obtained as a yellow powder with a yield of 67% (121 mg, 0.26 mmol).

1H NMR (CDCl3, 400 MHz): δ 1.44 (s, 9H); 1.60 (s, 9H); 2.95 (d, 3H, 3J=4.6 Hz); 4.39 (d, 2H, 3J=5.2 Hz); 4.82 (sl, 1H); 6.67 (sl, 1H); 8.48 (s, 1H); 13C NMR (CDCl3, 100 MHz): δ 28.1 (3C); 28.3 (4C); 47.6; 79.5; 82.9; 83.9; 113.1; 147.7; 154.9; 157.5; 158.3; 166.7.

Example 3.4: tert-butyl (6-iodo-1-methyl-2,4-dioxo-2,4-dihydro-1H-pyrido[2,3-d][1,3]oxazine-5-yl) methyl carbamate (18)

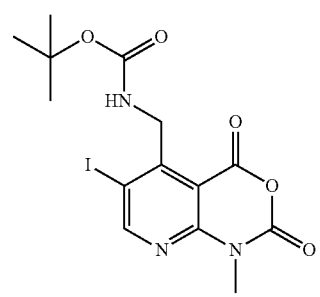

In a 25 ml flask under nitrogen, 100 mg 17 (0.22 mmol, 1 eq) are dissolved in 3 ml DCM. 342 µL phosgene (0.65 mmol, 20% in toluene, 3 eq) and 90 µL TEA (0.65 mmol, 3 eq) are added simultaneously and the reaction is stirred at room temperature for 30 min. This operation is repeated three times in order to convert all of the raw material. 30 ml water are then added and the solution is extracted with DCM (3×30 mL). The organic phases are then combined, dried over MgSO$_4$, and evaporated. The azaistoic anhydride 18 thus obtained is reacted directly with no additional purification step.

Example 4: Reaction of Molecules Derived from the Azaisatoic Anhydride of the Invention with an Amine Compound This example demonstrates that the molecules synthesized in Examples 1 to 3, respectively molecules 9, 13 and 18 react with an amine compound such as phenylethylamine.

Diagram 6 Opening the azaisatoic anhydrides 9, 13, and 18 of the invention using phenylethylamine.

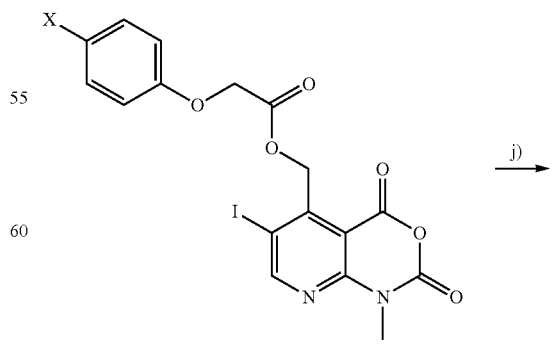

9 X = H
13 X = F

-continued

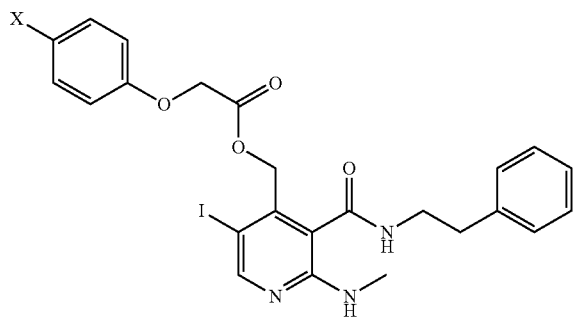

10 X = H
14 X = F

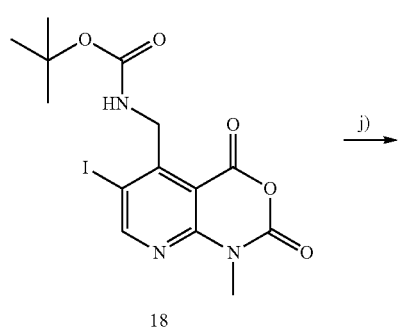

18 j) phenylethylamine, DCM, 1 h, rt.

Example 4.1: (5-iodo-2-(methylamino)-3-(phenethylcarbamoyl)pyridine-4-yl)methyl 2-phenoxyacetate (10)

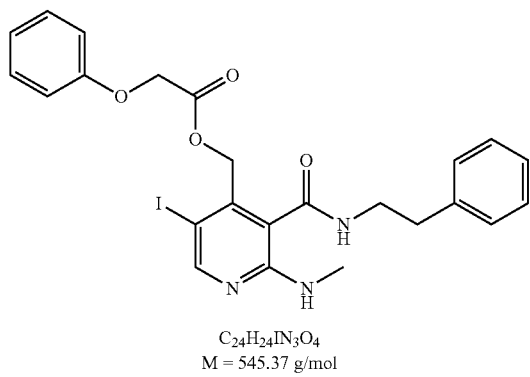 [SMILES: CNc1ncc(I)c(COC(=O)COc2ccccc2)c1C(=O)NCCc1ccccc1]

C$_{24}$H$_{24}$IN$_3$O$_4$
M = 545.37 g/mol

Into a 10 mL flask are added 65 mg 9 (0.13 mmol, 1 eq), 1 ml DCM, and 17.4 μL phenylethylamine (0.13 mmol, 1 eq) The reaction mixture is stirred for 1 h at room temperature. 15 ml water are then added and the solution is extracted with Et$_2$O (5×20 mL) The organic phases are then combined, dried over MgSO$_4$, and evaporated. The crude reaction product is then purified on a silica gel column using gradient elution (PE/AcOEt 9/1 to PE/AcOEt 7/3).

The final product is obtained as a yellowish powder with a yield of 71% (50 mg, 0.09 mmol).

Mp=164-166° C.; IR (KBr) ν (cm-1): 3428, 3296, 2924, 1761, 1627, 1433, 1170, 754, 1H NMR (CDCl3, 400 MHz): δ 2.86 (s, 3H); 2.88 (d, 2H, 3J=7.1 Hz); 3.69 (m, 2H); 4.57 (s, 2H); 4.98 (s, 2H); 5.58 (d, 1H, 3J=4.5 Hz); 6.54 (t, 1H, 3J=5.6 Hz); 6.88 (d, 2H, 3J=8.8 Hz); 7.00 (t, 1H, 3J=7.6 Hz); 7.21 (m, 2H); 7.28 (m, 5H); 8.40 (s, 1H); 13C NMR (CDCl3, 100 MHz): δ 28.4; 35.2; 40.6; 64.9; 67.3; 80.3; 114.6 (2C); 118.6; 122.0; 126.8; 128.6 (2C); 128.7 (2C), 129.7 (2C); 138.1; 140.7; 156.3; 156.8; 157.5; 166.5; 168.3.

Example 4.2: (5-iodo-2-(methylamino)-3-(phenethylcarbamoyl)pyridine-4-yl)methyl 2-(4-fluorophenoxy)acetate (14)

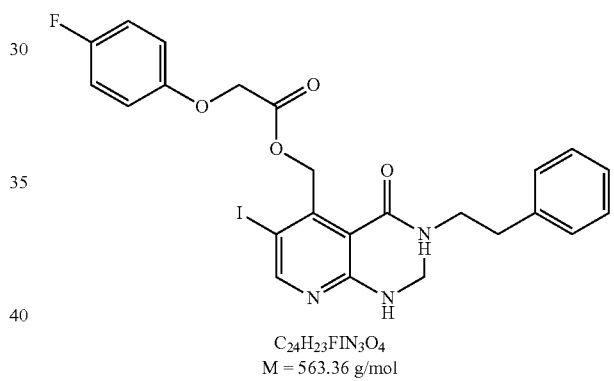

C$_{24}$H$_{23}$FIN$_3$O$_4$
M = 563.36 g/mol

Into a 10 mL flask are added 50 mg 13 (0.10 mmol, 1 eq), 1 ml DCM, and 12.9 μL phenylethylamine (0.10 mmol, 1 eq). The reaction is stirred at room temperature for 1 h. 10 mL water are then added and the solution is extracted with Et$_2$O (5×15 mL). The organic phases are then combined, dried over MgSO$_4$, and evaporated. The crude reaction product is then purified on a silica gel column using gradient elution (PE/AcOEt 7/3 to PE/AcOEt 6/4). The final product is obtained as a yellowish powder with a yield of 87% (50 mg, 0.09 mmol).

Mp=165-167° C.; IR (KBr): ν, 3388, 3376, 2924, 1742, 1661, 1577, 1504, 1191, 824; 1H NMR (CDCl3, 400 MHz): δ 2.86 (d, 3H, 3J=4.64 Hz); 2.89 (t, 2H, 3J=6.84 Hz); 3.72 (m, 2H); 4.51 (s, 2H); 4.99 (s, 2H); 5.55 (d, 1H, 3J=4.6 Hz); 6.51 (t, 1H, 3J=8.0 Hz); 6.83 (m, 2H); 6.97 (m, 2H); 7.21 (m, 3H); 7.30 (m, 2H); 8.40 (s, 1H); 13C NMR (CDCl3, 100 MHz): δ 28.4; 35.1; 40.5; 65.6; 67.3; 80.2; 115.9 (d, 3JC-F=8 Hz, 2C); 116.1 (d, 2JC-F=23 Hz, 2C); 118.6; 126.8; 128.6 (2C); 128.7 (2C); 138.1; 140.7; 153.6 (d, 4JC-F=2 Hz, 1C); 156.3; 156.8; 157.9 (d, 1JC-F=222 Hz, 1C); 166.5; 168.1.

Example 4.3: tert-butyl ((5-iodo-2-(methylamino)-3-(phenethylcarbamoyl)pyridine-4-yl)methyl)carbamate (19)

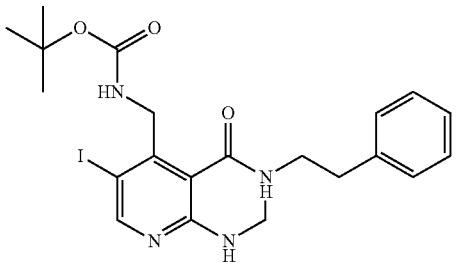

C$_{21}$H$_{27}$IN$_4$O$_3$
M = 510.37 g/mol

In a 10 mL flask, the azaisatoic anhydride 18 is dissolved in 1 mL DCM. 27.6 μL phenylethylamine (0.22 mmol, 1 eq) are then added and the reaction mixture is stirred at room temperature for 1 h. 10 mL water are then added and the solution is extracted with Et$_2$O (4×20 mL). The organic phases are then combined, dried over MgSO$_4$, and evaporated. The crude reaction product is then purified on a silica gel column using gradient elution (PE/AcOEt 7/3 to PE/AcOEt 4/6).

The final product is obtained as a yellowish powder with a yield of 54% (61 mg, 0.12 mmol).

1H NMR (CDCl3, 400 MHz): δ 1.34 (s, 9H); 2.79 (d, 3H, 3J=4.6 Hz), 2.88 (t, 2H, 3J=7.1 Hz); 3.67 (m, 2H); 3.87 (d, 2H, 3J=6.5 Hz); 5.47 (sl, 1H); 5.72 (sl, 1H) 7.18 (m, 5H); 8.27 (s, 1H); 8.98 (sl, 1H); 13C NMR (CDCl3, 100 MHz): δ 28.3 (3C); 28.4; 30.0; 40.6; 44.9; 80.0; 80.6; 118.9; 126.4; 128.4 (2C); 128.7 (2C), 138.8; 143.1; 156.1; 156.2; 156.7; 166.7.

Example 5: Method for the Deprotection of Aza-Anthranilate Compounds and Release of Phenylethylamine Under Hot Start PCR Conditions Here we demonstrate that the derivatives 10, 14, and 19 synthesized in Example 3 can be cleaved in hot start PCR conditions and release the phenylethylamine which mimics a protein.

General Procedure:

Into a 1.5 mL tube are added: 20 μL 2.5 mM amide solution (10, 14 or 19) in DMSO and 180 μL of a buffer conventionally used in a genetic material amplification reaction (60 mM Tris pH 9, 50 mM KO, 1 mM MgCl$_2$). The mixture is then stirred at 95° C. in a thermomixer. LCMS monitoring (condition 1) is performed at t=15 min, 30 min, and 1 h

Example 5.1: Evaluation of Cleavage at 95° C. of the Aza-Anthranilate Phenoxyacetate Derivative 10

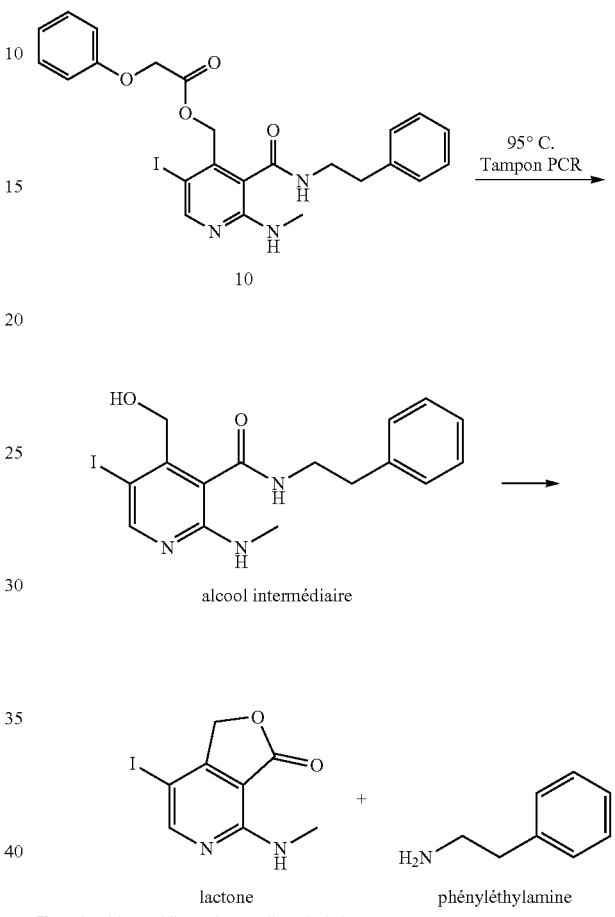

Diagram 7 Cleavage of aza-anthranilate compound 10 under hot start PCR conditions Key: alcool intermédiare = intermediate alcohol Thermal deprotection of the phenoxyacetate group leads to formation of the corresponding benzyl alcohol (see Diagram 7). The nucleophilic attack of alcohol on the carbonyl involved in the amide bond then allows releasing the phenylethylamine into the medium by generating the corresponding lactone.

Figure 1:
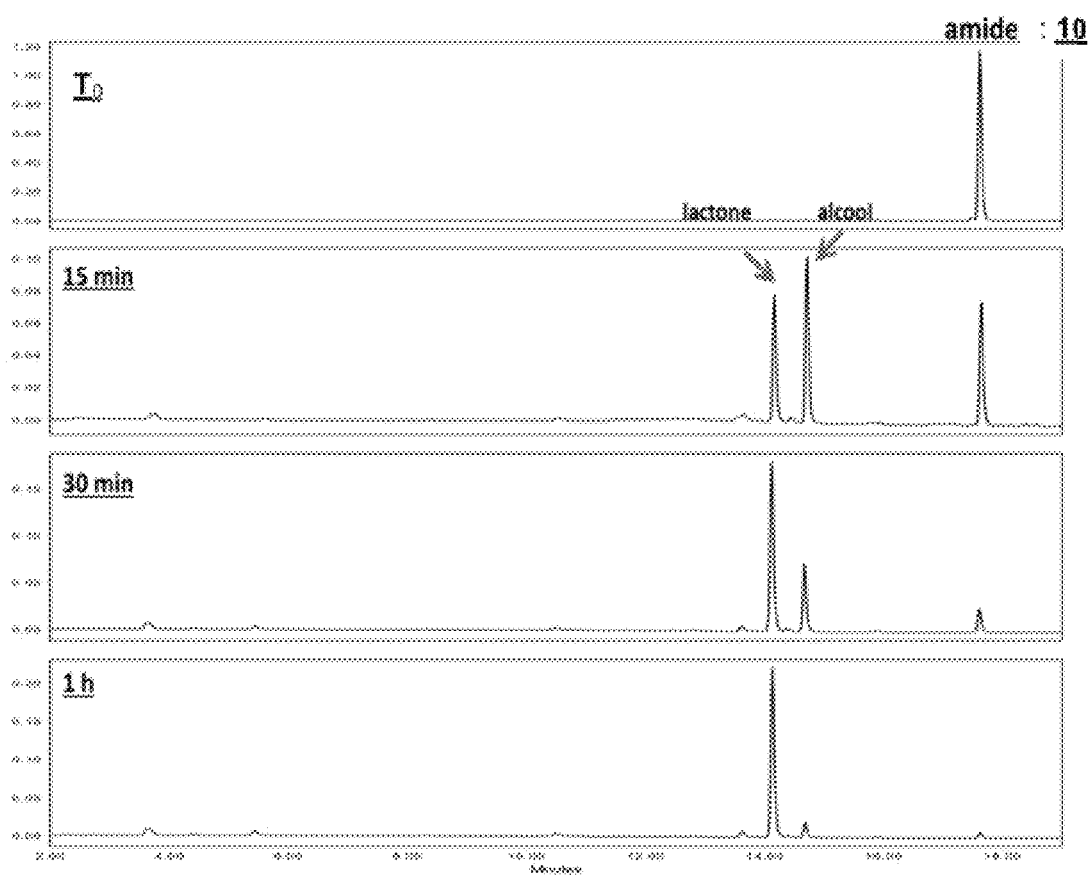
FIG. 1: HPLC monitoring of the cleavage of the phenoxyacetate aza-anthranilate derivative 10 and of the release of phenylethylamine.

This reaction cascade is shown in the HPLC chromatograms of FIG. 1.

After 15 minutes at 95° C., one will note the formation of the deprotected alcohol and the expected lactone which indicates the release of phenylethylamine. This result clearly demonstrates the thermolabile nature of the phenoxyacetate group resulting in the formation of the corresponding alcohol After cyclization, we find the presence of the expected lactone, demonstrating the cleavage of the amide bond and therefore the release of phenyethylamine into the medium. After 1 h at 95° C., the population of the initial amide and the alcohol have almost completely disappeared in favor of lactone.

This result demonstrates the possibility of cleaving an amide bond at 95° C. by this intramolecular cyclization system.

Example 5.2: Evaluation of Cleavage at 95° C. of the Fluorophenoxyacetate Aza-Anthranilate Derivative 14

FIG. 8 Cleavage of aza-anthranilate compounds 14 in hot start PCR conditions

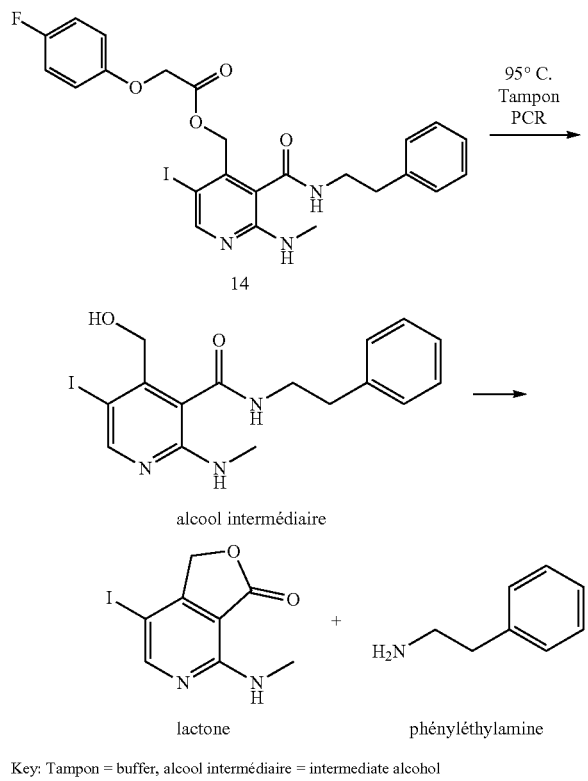

Key: Tampon = buffer, alcool intermédiaire = intermediate alcohol

Figure 2:
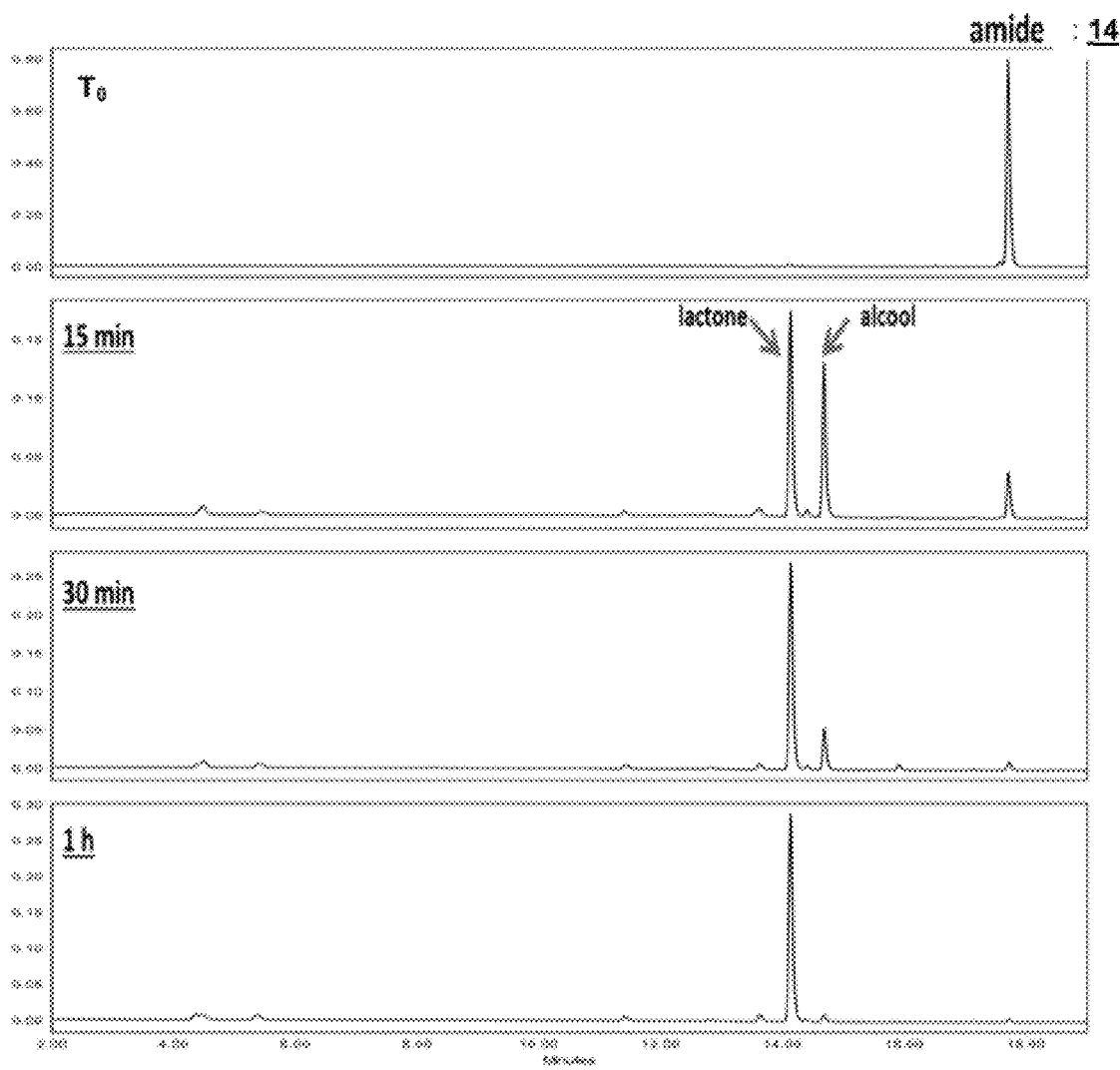
FIG. 2: HPLC monitoring of the cleavage of the fluorophenoxyacetate aza-anthranilate derivative 14 and of the release of phenylethylamine.

The deprotection method has also been implemented using the fluorophenoxyacetate derivative 14. After 15 minutes at 95° C., the amide population is very low. In particular, it is lower than the result observed with derivative 10 (see FIG. 2). The presence of the fluorine atom accelerates cleavage of the phenoxyacetate group. Therefore, after 30 minutes, this amide population has almost completely disappeared in favor of alcohol and a high predominance of lactone indicating the release of phenylethylamine.

Example 5.3: Evaluation of Cleavage at 95° C. of the N-Boc Aza-Anthranilate Derivative 19

Diagram 9 Cleavage of N—Boc aza-anthranilate compounds 19 in hot start PCR conditions

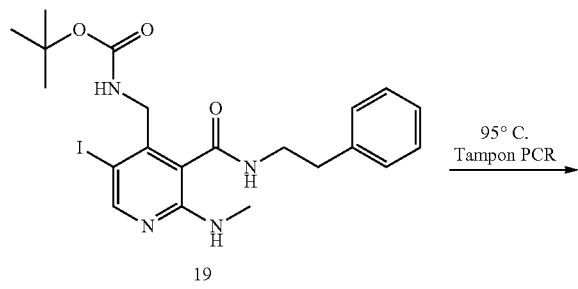

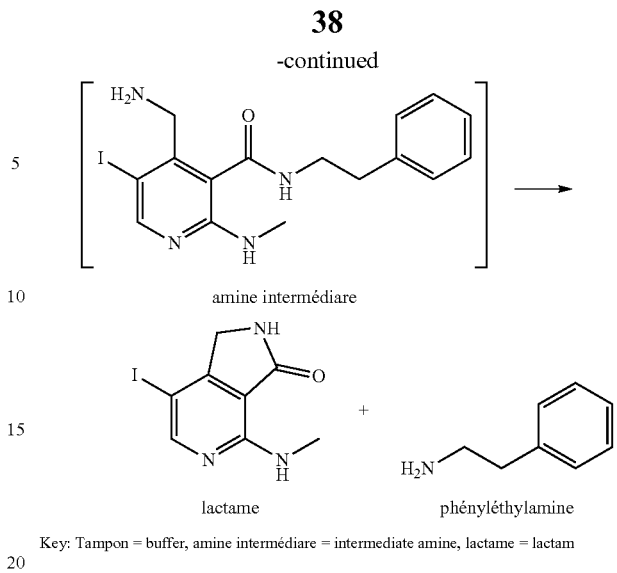

Key: Tampon = buffer, amine intermédiare = intermediate amine, lactame = lactam

In this case, the deprotection of the N-boc group leads to the benzyl amine intermediate derivative.

Figure 3:
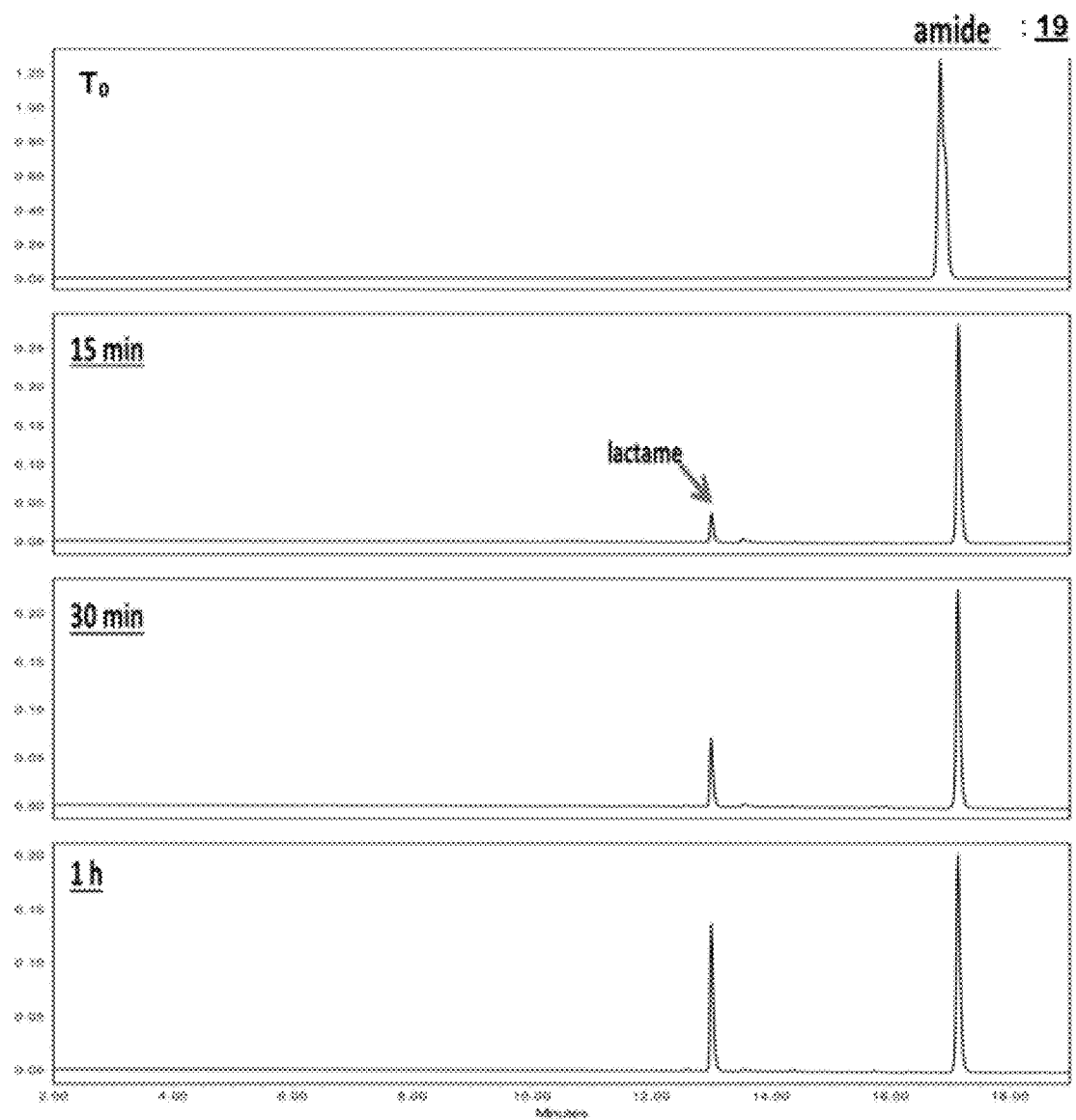
FIG. 3: HPLC monitoring of the cleavage of the N-Boc aza-anthranilate derivative 19 and of the release of phenylethylamine.

This derivative can then be cyclized to form the corresponding lactam by releasing phenylethylamine into the medium (Diagram 9 above). HPLC monitoring which shows the various intermediates is represented in FIG. 3.

For this derivative, the non-cyclized deprotected form (intermediate amine) is not detected. This example therefore demonstrates the immediate cyclization of the N-boc group after deprotection, to form phenylethylamine. This confirms the advantage of the amino functional group in position 5 in comparison to the alcohol functional group, for fast cyclization. The skilled person will therefore find the appropriate protecting group for the $NH_2$ functional group in position 5 of the aromatic ring, for obtaining a sufficiently rapid deprotection resulting in instantaneous cyclization and the release of phenylethylamine.

Example 6: Reversible Protection of Hemoglobin by the Azaisatoic Compound 13 as Described in the Invention We demonstrate here that the azaisatoic derivative 13 having the fluorophenoxy thermolabile group is capable of reacting with a protein under mild conditions in an aqueous medium in order to form a protein-fluorophenoxy aza anthranilate derivative.

The removal of this protecting group after heat treatment at 95° C. makes it possible to regenerate the native protein.

Protocol:

The mixtures are created as described below, where experiments AL600 1× to AL 600 0.25× respectively correspond to 33 µg hemoglobin reacted with increasing concentrations of the azaisatoic compound in a mixture of DMSO and PBS at pH 7.4 (PBS=Phosphate buffered saline resulting from dissolving a tablet, reference Sigma P4417, in 200 ml water (pH 7.4)) The mixtures are incubated at room temperature for 2 hours before collecting an aliquot for HPLC analysis on a Waters XBridge BEH C4 300 column (Milford. USA), with a gradient of 20 to 72% acetonitrile in a solution of 10 mM trifluoroacetic acid, at 120 min.

TABLE 1

Relative concentration of reagents for carrying out the reversible acylation of hemoglobin

| EXPERIMENTS | Human hemoglobin (Sigma H7379) 6.6 µg/µl in PBS µl | PBS pH 7.4 µl | DMSO µl | 13 (41 mM in DMSO) µl |
|---|---|---|---|---|
| AL 600 0.25x | 5 | 5 | 8.75 | 1.25 |
| AL 600 0.5x | 5 | 5 | 7.5 | 2.5 |
| AL 600 1x | 5 | 5 | 5 | 5 |
| CTRLS WITHOUT acylating reagent | | | | |
| AL 602 CTRL 0.25X | 5 | 5 | 10 | 0 |

Figure 4:
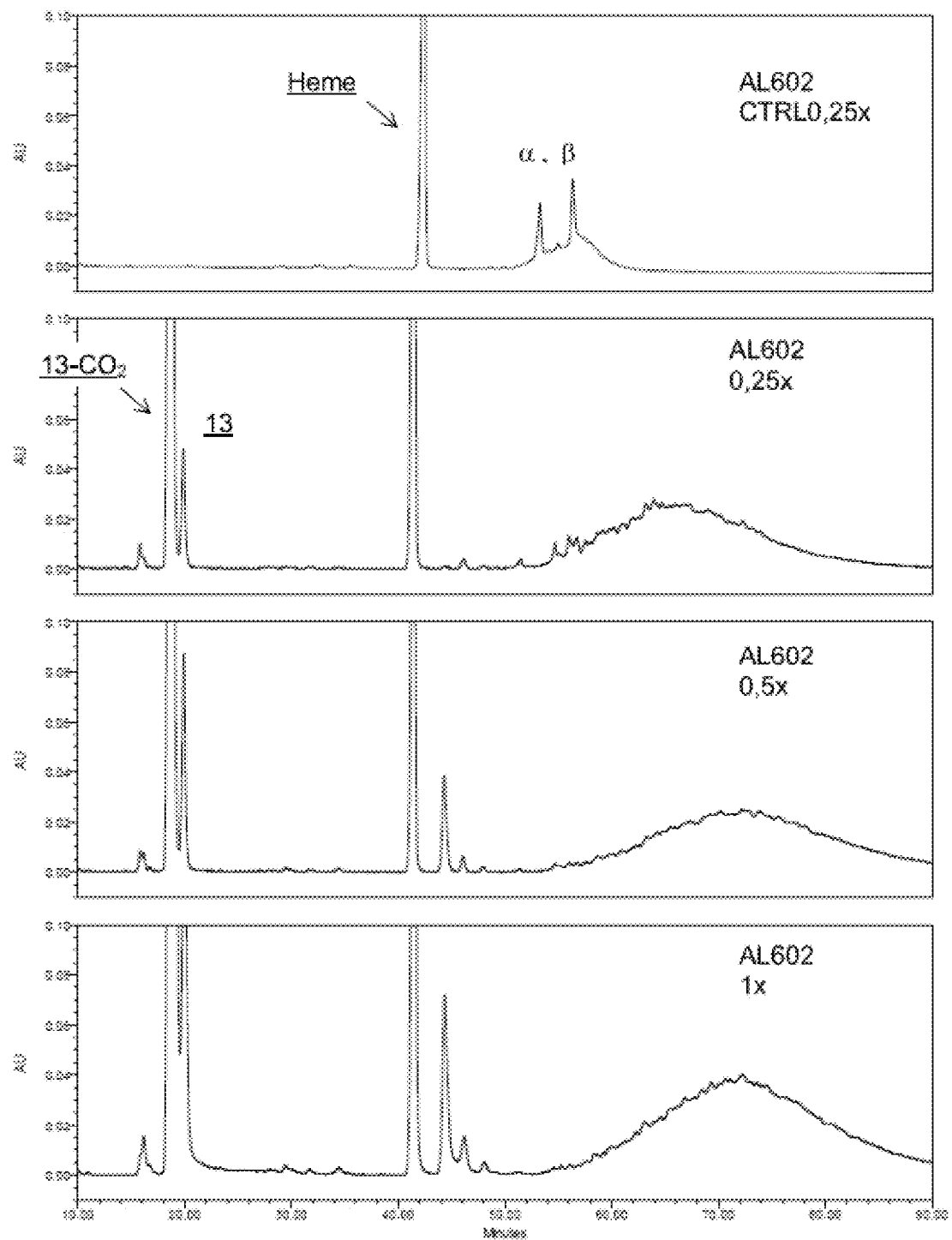
FIG. 4: Acylation of hemoglobin by compound 13 used at different concentrations.

In FIG. 4, the chromatogram AL602 CTRL 0.25× shows that the control hemoglobin has not reacted with the compound 13. One can see the heme and the two alpha and beta subunits of the protein portion. The following three chromatograms (AL 600 0.25×-1×) show the disappearance of the protein portion in favor of a massive shift to the right corresponding to the alpha and beta subunits acylated by the azaisatoic compound 13. The broadening of the peak corresponds to the random acylation of reactive sites of the protein.

It is thus demonstrated that the azaisatoic compound of the invention as described can react with a protein.

Figure 5:
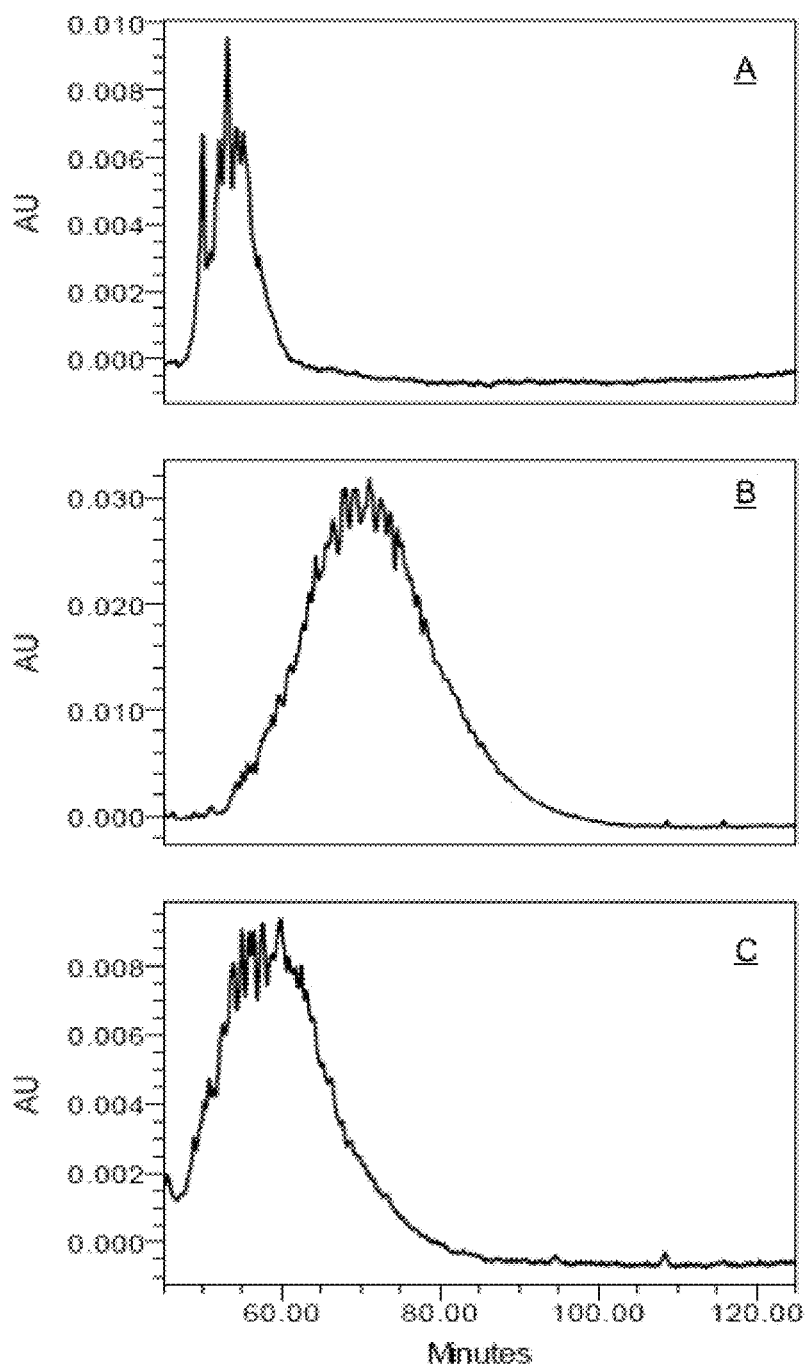
FIG. 5: Reversal of the acylation of the hemoglobin after heat treatment.

When the reaction medium AL 600 1× is subjected to heat treatment at 95° C. for 15 min in a PCR buffer (consisting primarily of Tris pH9), hydrolysis of the benzylamide portion is observed which leads to restoring the chromatographic profile of the native hemoglobin. This is visible in FIG. 5, where the top chromatogram (A) shows native hemoglobin taken up in 8M GuHCl, the middle chromatogram (B) shows hemoglobin acylated by compound 13 and taken up in 8M GuHCl. and the bottom chromatogram (C) shows hemoglobin acylated by compound 13 then heated in Tris buffer pH8 and taken up in 8M GuHCl. One can clearly see, as before, that acylation of the hemoglobin leads to formation of a mass of acylated protein and then this mass disappears after heat treatment in order to regenerate the native protein.

Note that the reaction media were taken up after reaction in 8M GuHCl in order to solubilize the protein portion that would have precipitated during heat treatment. This example demonstrates the reversible acylation of a model protein by compound 13 as described in the invention.

Example 7: Demonstration of Reversible Acylation of Taq Polymerase by the Azaisatoic Compound 13 as Described in the Invention Here we demonstrate that the azaisatoic derivative 13 having the thermolabile fluorophenoxy group is capable of reacting with a thermostable polymerase (Taq) under mild conditions and in an aqueous medium, to form a Taq-aza anthranilate fluorophenoxy derivative. The removal of this protecting group after heat treatment at 95° C. in PCR conditions makes it possible to restore the activity of the polymerase, which is demonstrated by measuring its activity.

The concept of using suitably modified azaisatoic anhydrides to temporarily mask the activity of a polymerase and then restore it after heat treatment is thus demonstrated.

Protocol:

We used the Genscript Taq (2500 u/100 µl REF E00012), but in order to eliminate all traces of nucleophiles in this enzyme we did a change of buffer beforehand by passing through an Amicon 10 KD microcon (no. 42407). The enzyme suspension was thus deposited on the microcon and centrifuged until buffer depletion Five washes were performed with 100 d PBS pH 7.4, then the last retentate was recovered by inverting the tube and made up to QSP 20 µl with PBS to obtain a suspension at 125 u/µl. We thus demonstrated that the Tris and glycerol were eliminated in a highly satisfactory manner by this method.

The mixtures as described in Table 2 are then created, where experiments AL604 0.25× to AL604 0.375× respectively correspond to 625 units of Taq polymerase reacted with increasing concentrations of the azaisatoic compound in a mixture of DMSO and PBS at pH 7.4 (PBS=Phosphate buffered saline resulting from dissolving a tablet, reference Sigma P4417, in 200 ml water (pH 7.4)). The mixtures are incubated at room temperature for 3 hours with light vortex mixing before assessing their enzymatic activity in hot start PCR conditions.

TABLE 2

Relative concentration of reagents for implementing, the reversible arylation of TAQ polymerase

| EXPERIMENTS | Genscript Taq (125 u/µl) Units/µl | PBS pH 7.4 µl | DMSO µl | 13 (41 mM in DMSO) µl | Final TAQ concentration (20 µl at 50/50 PBS/DMSO) u/µl |
|---|---|---|---|---|---|
| AL 604 0.25x | 625 u/5 µl | 5 | 8.75 | 1.25 | 31 |
| AL 604 0.375x | 625 u/5 µl | 5 | 8.1 | 1.9 | 31 |

Determination of Polymerase Activity of TAQ Modified by Compound 13:

The polymerization activity of the TAQ polymerase is determined using an oligonucleotide probe of 45 bases terminated by a "hairpin" structure. This is characterized by the presence of a fluorescence quencher at the beginning of the structure and a fluorophore at the end of the probe sequence, such that the quencher is spatially close to the fluorophore and no fluorescence signal can be measured in this configuration. Due to the action of the polymerase activity, this probe is elongated by means of an oligonucleotide of 19 bases complementary to the beginning of the previous probe. Due to the elongation action, the probe hairpin structure is unfolded and the fluorophore is able to emit, and fluorescence is then measurable. This fluorescence measurement is carried out at a temperature of 60° C. for 20 minutes in the presence of the reagents required for activity of the enzyme, meaning dNTP, MgCl2, and a basic buffer at pH 9.5.

The increase in fluorescence is linear at the start of the measurement and allows calculating an initial rate corresponding to the amount of fluorescence emitted per minutes of elongation By measuring the initial rate in U/IL for different concentrations of a given polymerase having a known activity, it is possible to establish a calibration curve that makes it possible to measure the activity of a similar enzyme of unknown activity.

Chemical modification of the polymerase to render it inactive is measured by this method. By measuring the level of residual activity after modification of the enzyme, it is possible to determine the effectiveness of the protection in place A polymerase completely inactivated by chemical

The invention claimed is:

1. A compound of the following formula (I):

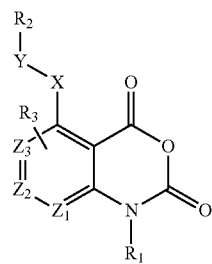

wherein

X is a covalent bond or a $C_1$-$C_4$ alkyl,

Y is a nucleophilic group selected from O, S, $NR_4$, O—$NR_4$, NH—O, NH—$NR_4$, C(O)—O—$NR_4$, C(O)—NH—O, C(O)—NH—$NR_4$, O—C(O)—NH—$NR_4$, NH—C(O)—NH—$NR_4$, O—C(O)—NH—O, NH—C(O)—NH—O, O—C(O)—O—$NR_4$, NH—C(O)—O—$NR_1$, or C(O)—S, in which $R_4$ is H or a $C_1$-$C_4$ alkyl group, with the proviso that when Y is O, S, or NH, X is not the covalent bond, $Z_1$, $Z_2$, $Z_3$ each represent, independently of one another, N or C, $R_1$ is H, a $C_1$-$C_6$ alkyl group, an alkenyl having 2 to 12 carbon atoms, an aryl group having 6 to 14 carbon atoms in the aromatic ring portion, or a heterocycle having 6 to 14 ring atoms in the ring portion, in which said alkyl, alkenyl, aryl, or heterocycle is optionally substituted one or more times by an amine, imine, nitrile, cyano, amide, imide, hydroxyl, alkoxyl, carbonyl, carboxyl, ester, thiol, thioether, thioester, or halide functional group, $R_2$ is a tert-butoxycarbonyl (BOC), substituted or unsubstituted phenoxyacetyl, trityl, methoxytrityl, dimethoxytrityl, or citraconyl group, $R_3$ is H, a $C_1$-$C_{12}$ alkyl group, an aryl group having 6 to 14 carbon atoms in the aromatic ring portion, a heterocycle having 6 to 14 ring atoms in the ring portion, an acyl group having 2 to 12 carbon atoms, an alkenyl group having 2 to 12 carbon atoms, a halogen, or a cyano group, in which said alkyl, alkenyl, aryl, or heterocycle is optionally substituted one or more times by an amine, imine, nitrile, cyano, amide, imide, hydroxyl, alkoxyl, carbonyl, carboxyl, ester, thiol, thioether, thioester, or halide functional group.

2. The compound according to claim 1, wherein the compound is of the following formula (II):

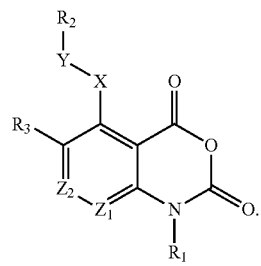

3. The compound according to claim 1, wherein $R_1$ is a methyl group.

4. The compound according to claim 1, wherein $R_3$ is iodine.

5. The compound according to claim 1, wherein $Z_1$ is N and $Z_2$ is C.

6. The compound according to claim 1, wherein the compound has one of the following structures:

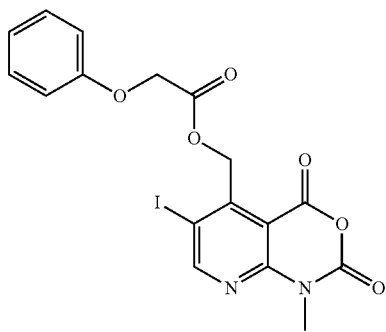

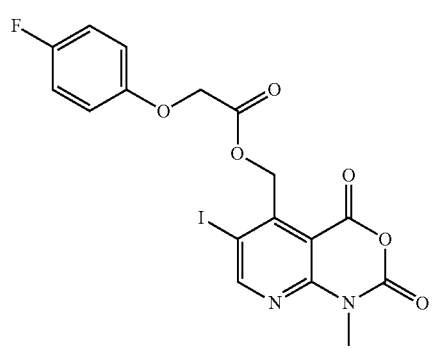

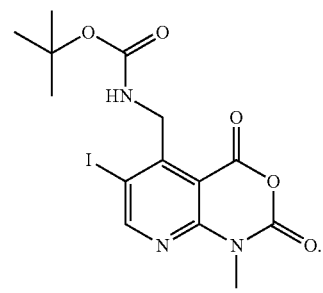

7. The compound according to claim 2, wherein $R_1$ is a methyl group.

8. The compound according to claim 2, wherein $R_3$ is iodine.

9. The compound according to claim 2, wherein $Z_1$ is N and $Z_2$ is C.

10. The compound according to claim 7, wherein $R_3$ is iodine.

11. The compound according to claim 7, wherein $Z_1$ is N and $Z_2$ is C.

12. The compound according to claim 8, wherein $Z_1$ is N and $Z_2$ is C.

13. The compound according to claim 10, wherein $Z_1$ is N and $Z_2$ is C.

14. The compound according to claim 1, wherein the compound has the following structure:

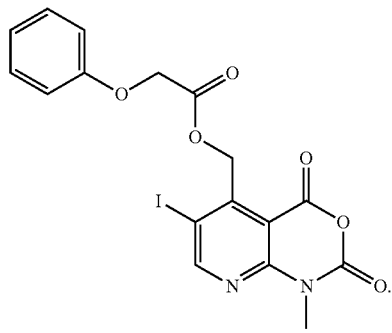

(IV)

15. The compound according to claim 1, wherein the compound has the following structure:

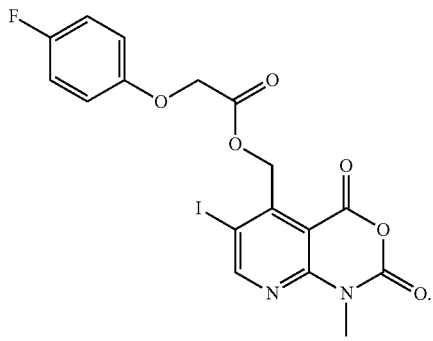

(V)

16. The compound according to claim 1, wherein the compound has the following structure:

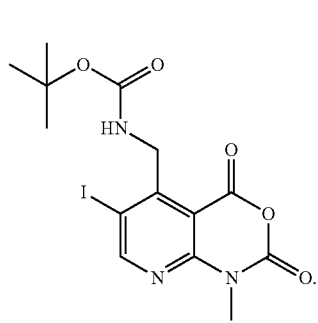

(VI)

* * * * *